US006124273A

United States Patent [19]
Drohan et al.

[11] Patent Number: 6,124,273
[45] Date of Patent: *Sep. 26, 2000

[54] CHITIN HYDROGELS, METHODS OF THEIR PRODUCTION AND USE

[75] Inventors: William N. Drohan, Springfield, Va.; Martin J. MacPhee; Shirley I. Miekka, both of Gaithersburg, Md.; Manish S. Singh, Columbia, Md.; Clive Elson, Halifax, Canada; John R. Taylor, Jr., New York, N.Y.

[73] Assignees: Chitogenics, Inc., Morristown, N.J.; The American National Red Cross, Washington, D.C.; Coalition for Hemophilia B, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/960,555

[22] Filed: Oct. 13, 1997

Related U.S. Application Data

[63] Continuation of application No. 08/659,999, Jun. 7, 1996, abandoned.
[60] Provisional application No. 60/000,109, Jun. 9, 1995.

[51] Int. Cl.$^7$ .................................................. A61K 31/73
[52] U.S. Cl. ................................... 514/55; 514/2; 536/20
[58] Field of Search ........................... 514/2, 55; 536/20

[56] References Cited

U.S. PATENT DOCUMENTS

| | | | |
|---|---|---|---|
| Re. 33,375 | 10/1990 | Luck et al. | 514/2 |
| 4,424,346 | 1/1984 | Hall et al. | 536/20 |
| 4,570,629 | 2/1986 | Widra | 604/304 |
| 4,619,995 | 10/1986 | Hayes | 536/20 |
| 4,659,700 | 4/1987 | Jackson | 514/55 |
| 4,868,113 | 9/1989 | Jaye et al. | 435/70 |
| 4,886,787 | 12/1989 | de Belder et al. | 514/57 |
| 4,978,332 | 12/1990 | Luck et al. | 604/19 |
| 5,080,893 | 1/1992 | Goldberg et al. | 514/57 |
| 5,093,319 | 3/1992 | Higham et al. | 514/55 |
| 5,234,915 | 8/1993 | Mathur et al. | 514/57 |
| 5,460,939 | 10/1995 | Hansbrough et al. | 435/1.1 |
| 5,470,829 | 11/1995 | Prisell et al. | 514/12 |
| 5,510,102 | 4/1996 | Cochrum | 424/78.08 |
| 5,679,658 | 10/1997 | Elson | 514/55 |

FOREIGN PATENT DOCUMENTS

| | | |
|---|---|---|
| 0 312 208 | 4/1989 | European Pat. Off. . |
| 0 368 253 | 5/1990 | European Pat. Off. . |
| 0 637 450 | 2/1995 | European Pat. Off. . |
| 0 650 999 | 5/1995 | European Pat. Off. . |
| WO 96/13282 | 5/1996 | WIPO . |
| WO 96/13284 | 5/1996 | WIPO . |

OTHER PUBLICATIONS

Adelmann–Grill, B. C. et al., "Chemotactic migration of normal dermal fibroblasts towards epidermal growth factor and its modulation by platelet–derived growth factor and transforming growth factor–beta," *Eur. J. Cell Biol.* 51(2):322–326 (Apr. 1990).

Buchholz, H. W. et al., "Management of Deep Infection of Total Hip Replacement," *J. Bone and Joint Surgery* 63–B(3):342–353 (1981).

Buchholz, H. W. et al., "Antibiotic–loaded Acrylic Cement: Current Concepts," *Clin. Orthop. Rel. Res.* 190:96–108 (Nov. 1984).

Burgess, W. H. and T. Maciag, "The Heparin–Binding (Fibroblast) Growth Factor Family of Proteins," *Annu. Rev. Biochem* 58:575–606 (1989).

Canalis, E. et al., "Growth Factors and the Regulation of Bone Remodeling," *J. Clin. Invest.* 81(2):277–281 (Feb. 1988).

Chandrasekaran, S. K. and D. R. Paul, "Dissolution–Controlled Transport from Dispersed Matrixes," *J. Pharm. Sci.* 71(12):1399–1402 (Dec. 1982).

Chandy, T. and C. P. Sharma, "Biodegradable Chitosan Matrix for the Controlled Release of Steroids," *Biomat., Art. Cells & Immob. Biotech.* 19(14):745–760 (1991).

Christian, E. P. et al., "Reconstruction of Large Diaphyseal Defects, without Free Fibular Transfer, in Grade–IIIB Tibial Fractures," *J. Bone Joint Surgery* 71–A(7):994–1004 (Aug. 1989).

Dash, A. K, and R. Suryanarayanan, "An Implantable Dosage Form for the Treatment of Bone Infections," *Pharm. Res.* 9(8):993–1002 (Aug. 1992).

Golub, L. M. et al., "Treating Periodontal Diseases by Blocking Tissue–Destructive Enzymes," *J. Amer. Dent. Assoc.* 125:163–171 (Feb. 1994).

Goodson, J. M. et al., "Monolithic Tetracycline–containing Fibers for Controlled Delivery to Periodontal Pockets," *J. Periodontol.* 54(10):575–579 (Oct. 1983).

Gospodarowicz, D. et al., "Fibroblast growth factor," *Mol. Cell. Endocrinol.* 46(3):187–204 (1986).

Gospodarowicz, D. et al., "Structural Characterization and Biological Functions of Fibroblast Growth Factor," *Endocrine Rev.* 8(2):95–114 (1987).

Greco, F. et al., "Fibrin–antibiotic mixtures: An in vitro study assessing the possibility of using a biologic carrier for local drug delivery," *J. Biomed. Mat. Res.* 25(1):39–51 (Jan. 1991).

Greenhalgh, D. G. et al., "PDGF and FGF Stimulate Wound Healing in the Genetically Diabetic Mouse," *Amer. J. Pathol.* 136(6):1235–1246 (Jun. 1990).

(List continued on next page.)

*Primary Examiner*—Kathleen K. Fonda
*Attorney, Agent, or Firm*—Lahive & Cockfield, LLP

[57] ABSTRACT

This invention is directed to the preparation and utilization of supplemented chitin hydrogels, such as chitosan hydrogels. Further provided are biomaterials comprising same. The particular supplement delivered by the chitin hydrogel is selected as a function of its intended use. In one embodiment, this invention provides a composition of matter, comprising a chitin hydrogel or chitin-derived hydrogel, wherein the hydrogel does not inhibit full-thickness skin wound healing.

32 Claims, 3 Drawing Sheets

OTHER PUBLICATIONS

Gristina, A. G. et al., "Bacteria and Biomaterials," in: *Implantation Biology: The Host Response and Biomedical Devices*, Greco, R. S., ed., Boca Raton, FA: CRC Press, pp. 131–148 (Mar. 1994).

Hattori, T., "Experimental Investigations of Osteogenesis and Chondrogenesis by Implant of BMP–Fibrin Glue Mixture," *J. Jpn. Orthop. Assoc.* 64(9):824–834 (Sep. 1990).

Hauschka, P. V. et al., "Growth Factors in Bone Matrix: Isolation of Multiple Types by Affinity Chromatography on Heparin–Sepharose," *J. Biol. Chem.* 261(27):12665–12674 (Sep. 1986).

Hayek, A. et al., "An In Vivo Model for Study of the Angiogenic Effects of Basic Fibroblast Growth Factor," *Biochem. Biophys. Res. Comm.* 147(2):876–880 (Sep. 1987).

Higuchi, T., "Mechanism of Sustained–Action Medication: Theroetical Analysis of Rate of Release of Solid Drugs Disperesed in Solid Matrices," *J. Pharm. Sci.* 52(12):1145–1149 (Dec. 1963).

Jaye, M. et al., "Biological Equivalence of Natural Bovine and Recombinant Human α–Endothelial Cell Growth Factors," *J. Biol. Chem.* 262(34):16612–16617 (Dec. 1987).

Kawamura, M. and M. R. Urist, "Human Fibrin Is a Physiological Delivery System for Bone Morphogenetic Protein," *Clin. Orthop. Rel. Res.* 235:302–310 (Oct. 1988).

Klokkevold, P. R. et al., "Effect of Chitosan on Lingual Hemostasis in Rabbits With Platelet Dysfunction Induced by Epoprostenol," *J. Oral. Maxillofac. Surg.* 50(1):41–45 (Jan. 1992).

Knighton, D. R. et al., "Classification and Treatment of Chronic Nonhealing Wounds:Successful Treatment with Autologous Platelet–dervived Wound Healing Factors (PDWHF)," *Ann. Surg.* 204(3):322–330 (Sep. 1986).

Kram, H. B. et al., "Antibacterial Effects of Fibrin Glue–Antibiotic Mixtures," *J. Surg. Res.* 50(2):175–178 (Feb. 1991).

Fristl, J. et al., "Hydrocolloids and gels of chitosan as drug carriers," *Int. J. Pharm.* 99:13–19 (1993).

Ksander, G. A. et al., "The effect of platelet releasate on wound healing in animal models," *J. Amer. Acad. Dermatol.* 22(5):781–791 (May 1990).

Lynch, S. E. et al., "Growth Factors in Wound Healing: Single and Synergistic Effects on Partial Thickness Porcine Skin Wounds," *J. Clin. Invest.* 84(2):640–646 (Aug. 1989).

Stiles, C. D. et al., "Dual control of cell growth by somatomedins and platelet–derived growth factor," *Proc. Natl. Acad. Sci. USA* 76(3):1279–1283 (Mar. 1979).

Luyten, F. P. et al., "Purification and Partial Amno Acid Sequence of Osteogenin, a Protein Initiating Bone Differentiation," *J. Biol. Chem.* 264(23):13377–13380 (Aug. 1989).

Mackey, D. et al., "Antibiotic Loaded Plaster of Paris Pellets: An In vitro Study of a Possible Method of Local Antibiotic Therapy in Bone Infection," *Clin. Orthop. Rel. Res.* 167:263–268 (Jul. 1982).

Majid, S. A. et al., "Gentamicin–PMMA beads in the treatment of chronic osteomyelitis," *Acta Orthop. Scand.* 56(3):265–268 (Jun. 1985).

Menaché, D. et al., "Coagulation Factor IX (human)," in: *Hemophilia and Von Willebrand's Disease in the 1990's: A New Decade of Hopes and Challenges*, Lusher, J. M. and C. M. Kessler, eds., Amsterdam: Elsevier Science Publishers B. V., pp. 301–305 (1991).

Miclau, T. et al., "In Vitro Pharmocokinetics of Antibiotic Release from Locally Implantable Materials," *J. Orthop. Res.* 11(5):627–653 (1993).

Piszkiewicz, D. et al., "Inactivation of HIV in antithrombin–III concentrate by pasteurization," *Transfusion* 28(2):198–199 (1988).

Puumala, M. et al., "Intraventicular infusion of HBGF–2 promotes cerebral angiogenesis in Wistar rat," *Brain Res.* 534(1/2):283–286 (1990).

Rath, N. C. and A. H. Reddi, "Collagenous bone matrix is a local mitogen," *Nature* 278:855–857 (Apr. 1979).

Redl, H. et al., "In vitro properties of mixtures of fibrin seal and antibiotics," *Biomat.* 4(1):29–32 (Jan. 1983).

Sakurai, T. et al., "Controlled release of sisomicin from fibrin glue," *J. Controlled Rel.* 18(1):39–43 (1992).

Schlag, G. and H. Redl, "Fibrin Sealant in Orthopedic Surgery," *Clin. Orthop. Rel. Res.* 227:269–285 (Feb. 1988).

Schultz, G. S. et al., "Epithelial Wound Healing Enhanced by Transforming Growth Factor–α and Vaccinia Growth Factor," *Science* 235:350–235 (Jan. 1987).

Schrenk, P. et al., "Fibrin Glue Coating of e–PTFE Prostheses Enhances Seeding of Human Endothelial Cells," *Thorac. Cardiovasc. Surgeon* 35(1):6–10 (Feb. 1987).

Schwarz, N. et al., "The Influence of Fibrin Sealant on Demineralized Bone Matrix–Dependent Osteoinduction," *Clin. Orthop. Rel. Res.* 238:282–287 (Jan. 1989).

Tabor, E. et al., "Inactivation of Hepatitis B Virus by Heat in Antithrombin III Stabilized with Citrate," *Thromb. Res.* 22(1/2):233–238 (1981).

Thacharodi, D. and K. Panduranga Rao, "Release of nifedipine through crosslinked chitosan membranes," *Int. J. Pharm.* 96(1–3):33–39 (Jul. 1993).

Thompson, J. A. et al., "Site–Directed Neovessel Formation in Vivo," *Science* 241:1349–1352 (Sep. 1988).

Thompson, J. A. et al., "Heparin–binding growth factor I induces the formation of organoid neovascular structures in vivo," *Proc. Natl. Acad. Sci. USA* 86(20):7928–7932 (Oct. 1989).

Toriumi, D. M. et al., "Demineralized Bone: Implant Resorption With Long–Term Follow–up," *Arch. Otolaryngol. Head Neck Surg.* 116(6):676–680 (Jun. 1990).

Tsuboi, R. and D. B. Rifkin, "Recombinant Basic Fibroblast Growth Factor Stimulates Wound Healing in Healing–impaired db/db Mice," *J. Exp. Med.* 172(1):245–251 (Jul. 1990).

Urist, M. R. and B. S. States, "Bone Formation in Implants of Partially and Wholly Demineralized Bone Matrix Including Observations on Acetone–fixed Intra and Extracellular Proteins," *Clin. Orthop. Rel. Res.* 71:271–278 (Jul.–Aug. 1970).

Urist, M. R. et al., "Bone Morphogenesis in Implants of Insoluble Bone Gelatin," *Proc. Natl. Acad. Sci. USA* 70(12):3511–3515 (Dec. 1973).

Van Brunt, J. and A. Klausner, "Growth Factors Speed Wound Healing," *Bio/Technol.* 6(1):25–29 (Jan. 1988).

Wang, E. A. et al., "Bone Morphogenetic Proteins and Bone Repair," *J. Cell. Biochem. Suppl.* 15F:161 Abstract Q 020 (Apr. 1991).

Zilla, P. et al., "Use of fibrin glue as a substrate for in vitro endothelialization of PTFE vascular grafts," *Surgery* 105(4):515–522 (Apr. 1989).

English language abstract of EP 0 650 999 (Document AO1) from Derwent World Patents Index, WPI Acc. No. 95–163403/22 May 1995.

Borah et al. (Apr. 1995) "Wound Epithelialization is Accelerated by N,O–Carboxymethyl Chitosan" *Amereican Burn Assoc. 27th Annual Mtg.*, Alberquerque, NM.

Davies et al., (Aug. 1988) "N,O–Carboxymethl Chitosan, A New Water Soluble Chitin Derivative" Proceed. Int'l Chitin–Chitosan Conference.

McDermott et al. (1986) "Experimental Use of a New Gentamycin Impregnated Gel" Canadian Medical Assoc. Conference Abstract.

Menon et al. (Apr. 1995) "Development of a Composite of Hydroxylapatite and Chitosan as a Bone Graft Substitute" Proceedings of the 14th southern biomedical Engineering Conference, Shreveport, LA.

Schultz et al. (Jan. 1987) "Epithelial Wound Healing Enhanced by Transforming Growth Factor–$\alpha$ and Vaccinia Growth Factor" *Science* 235:350–352.

CHITIN HYDROGELS, METHODS OF THEIR PRODUCTION AND USE

This application is a continuation of application Ser. No. 08/659,999 filed Jun. 7, 1996, now abandoned, which claims benefit under 35U.S.C. 119(e) of provisional application 60/000,109, filed Jun. 9, 1995.

FIELD OF INVENTION

This invention is directed to the preparation and utilization of supplemented chitin hydrogels, such as chitosan hydrogels. Further provided are biomaterials comprising same. The particular supplement delivered by the chitin hydrogel is selected as a function of its intended use.

BACKGROUND OF THE INVENTION

Chitin (or a derivative thereof) is a polysaccharide composition prepared from the shells of arthropods, including crustaceans or insects. The material is biocompatible and naturally resorbed by the body, and has been previously used for sustained drug release, bone induction and hemostasis (Chandy and Sharma, *Biomat. Art. Cells & Immob. Biotech.* 19:745–760 (1991); Klokkevold, P. et al., *J. Oral Maxillofac. Sur.* 50:41–45 (1992)).

Surgical adhesives and tissue sealants have been used for sealing internal and external wounds, such as in bones and skin, to reduce blood loss and maintain hemostasis. Biologically-derived tissue sealants typically contain blood clotting factors and other blood proteins. One type of tissue sealant, referred to as fibrin sealant or fibrin glue, is a gel similar to a natural blood clot which is prepared from plasma. The precise components used to produce a specific fibrin sealant are a function of the particular plasma fraction which is used as a starting material; however, typically fibrin glue contains a mixture of proteins which disadvantageously include thrombin and traces of albumin, fibronectin and plasminogen, which upon contact are destructive of certain classes of plasma proteins, e.g., Factor IX. In addition, bioadhesives have proven unsuccessful in part because in many cases commercially available preparations of fibrin glue and tissue sealants are too dense to allow cell migration into and through the material to permit satisfactory wound healing. This limits their effectiveness in many in vivo uses for which a long-felt need remained until the discovery of the present chitin hydrogel as an effective delivery system a. Plasma Proteins Plasma proteins are any protein found within the plasma of a patient, or which is found in the plasma of a normal individual or animal, but which is absent or deficient in the patient (e.g, hemophilias). Particularly relevant to the present invention are plasma protein members of the blood clotting cascade, including those clotting factors which are thrombin sensitive; that is, those blood clotting factor molecules which have been shown to include one or more binding sites for thrombin. All coagulation proteins (e.g., Factors VIII, IX, VIIa, Protein C) have short circulating half-lives. Upon exposure to circulating thrombin, the thrombin-sensitive plasma proteins, such as Factor IX and possibly Factor VIII are soon inactivated.

The chitin hydrogel of the present invention, however, provides an effective system for the delivery of intact plasma proteins, including thrombin-sensitive plasma proteins. Plasma proteins include, but are not limited to, the following: albumin; immunoglobulins, including immunoglobulin A, M and G; fibrinogen; coagulation factors, including Factors II, VII, VIII, IX, X and XIII; plasminogen; protein C; protein S; plasma proteinase inhibitors, including antithrombin III, α1-antitrypsin, α2-macroglobulin, and C1 esterase inhibitor; α1-acid glycoprotein; ceruloplasmin; haptoglobin; transferrin; complement components C1 through C9; C4b binding protein; interalpha-trypsin inhibitor; apolipoproteins, including A-1, A-11, B, C and E; fibronectin and angiostatin.

b. Growth Factors

When a tissue is injured, polypeptide growth factors, which exhibit an array of biological activities, are released into the wound where they play a crucial role in healing (see, e.g., *Hormonal Proteins and Peptides* (Li, C. H., ed.) Volume 7, Academic Press, Inc., New York, N.Y. pp. 231–277 (1979) and Brunt et al., *Biotechnology* 6:25–30 (1988)). These activities include recruiting cells, such as leukocytes and fibroblasts, into the injured area, and inducing cell proliferation and differentiation. Growth factors that may participate in wound healing include, but are not limited to: platelet-derived growth factors (PDGFs); insulin-binding growth factor-1 (IGF-1); insulin-binding growth factor-2 (IGF-2); epidermal growth factor (EGF); transforming growth factor-α (TGF-α); transforming growth factor-β (TGF-β); platelet factor 4 (PF-4); and heparin binding growth factors one and two (HBGF-1 and HBGF-2, respectively).

PDGFs are stored in the alpha granules of circulating platelets and are released at wound sites during blood clotting (see, e.g., Lynch et al., *J. Clin. Invest.* 84:640–646 (1989)). PDGFs include: PDGF; platelet derived angiogenesis factor (PDAF); TGF-β; and PF4, which is a chemoattractant for neutrophils (Knighton et al., in *Growth Factors and Other Aspects of Wound Healing: Biological and Clinical Implications*, Alan R. Liss, Inc., New York, N.Y., pp. 319–329 (1988)). PDGF is a mitogen, chemoattractant and a stimulator of protein synthesis in cells of mesenchymal origin, including fibroblasts and smooth muscle cells. PDGF is also a nonmitogenic chemoattractant for endothelial cells (see, for example, Adelmann-Grill et al., *Eur. J. Cell Biol.* 51:322–326 (1990)).

IGF-1 acts in combination with PDGF to promote mitogenesis and protein synthesis in mesenchymal cells in culture. Application of either PDGF or IGF-1 alone to skin wounds does not enhance healing, but application of both factors together appears to promote connective tissue and epithelial tissue growth (Lynch et al., *Proc. Natl. Acad. Sci.* 76:1279–1283 (1987)).

TGF-β is a chemoattractant for macrophages and monocytes. Depending upon the presence or absence of other growth factors, TGF-β may stimulate or inhibit the growth of many cell types.

Other growth factors, such as EGF, TGF-α, the HBGFs and osteogenin are also important in wound healing. Topical application of EGF accelerates the rate of healing of partial thickness wounds in humans (Schultz et al., *Science* 235:350–352 (1987)). Osteogenin, which has been purified from demineralized bone, appears to promote bone growth (see, e.g., Luyten et al., *J. Biol. Chem.* 264:13377 (1989)). In addition, platelet-derived wound healing formula, a platelet extract which is in the form of a salve or ointment for topical application, has been described (see, e.g., Knighton et al., *Ann. Surg.* 204:322–330 (1986)).

The heparin binding growth factors (HBGFs), including the fibroblast growth factors (FGFs), which include acidic HBGF (aHBGF also known as HBFG-1 or FGF-1) and basic HBGF (bHBGF also known as HBGF-2 or FGF-2), are potent mitogens for cells of mesodermal and neuroectodermal lineages, including endothelial cells (see, e.g., Burgess et al., *Ann. Rev. Biochem.* 58:575–606 (1989)). In addition, HBGF-1 is chemotactic for endothelial cells and astroglial cells. Both HBGF-1 and HBGF-2 bind to heparin, which protects them from proteolytic degradation. The array of biological activities exhibited by the HBGFs suggests that they play an important role in wound healing.

Basic fibroblast growth factor (FGF-2) is a potent stimulator of angiogenesis and the migration and proliferation of fibroblasts (see, for example, Gospodarowicz et al., *Mol. Cell. Endocinol.* 46:187–204 (1986) and Gospodarowicz et al., *Endo. Rev.* 8:95–114 (1985)). Acidic fibroblast growth factor (FGF-1) has been shown to be a potent angiogenic factor for endothelial cells (Burgess et al., supra, 1989). Other FGF's may be chemotactic for fibroblasts. Growth factors are, therefore, potentially useful for specifically promoting wound healing and tissue repair.

However, to date, the art has provided inadequate means for applying a growth factor to a wound to achieve a prolonged contact between the wound and the growth factor. This problem has been overcome by the chitin hydrogel of the present invention.

c. Bone Wounds and Their Repair

The sequence of bone induction was first described by Urist et al. using demineralized cortical bone matrix (*Clin. Orthop. Rel. Res.* 71:271 (1970) and *Proc. Natl. Acad. Sci. USA* 70:3511 (1973)). Implanted subcutaneously in allogeneic recipients, demineralized cortical bone matrix releases factors which act as local mitogens to stimulate the proliferation of mesenchymal cells (Rath et al., *Nature (Lond.)* 278:855 (1979)). New bone formation occurs between 12 and 18 days postimplantation. Ossicle development replete with hematopoietic marrow lineage occurred by day 21 (Reddi, A., In *Extracellular Matrix Biochemistry* (Piez et al., ed.) Elsevier, New York, N.Y., pp. 375–412 (1984)).

Demineralized bone matrix (DBM) is a source of osteoinductive proteins known as bone morphogenetic proteins (BMP), and growth factors which modulate the proliferation of progenitor bone cells (see, e.g., Hauschka et al., *J. Biol. Chem.* 261:12665–12674 (1986) and Canalis et al., *J. Clin. Invest.* 81:277–281 (1988)). Eight BMPs have now been identified and are abbreviated BMP-1 through BMP-8. BMP-3 and BMP-7 are also known as osteogenin and osteogenic protein-1 (OP-1), respectively.

Unfortunately, DBM materials have little clinical use unless combined with particulate marrow autografts. There is a limit to the quantity of DBM that can be surgically placed into a recipient's bone to produce a therapeutic effect. In addition, resorption has been reported to be at least 49% (Toriumi et al., *Arch. Otolaryngo. Head Neck Surg.* 116:676–680 (1990)).

DBM powder and osteogenin may be washed away by tissue fluids before their osteoinductive potential is expressed. In addition, seepage of tissue fluids into DBM-packed bone cavities or soft-tissue collapse into the wound bed are two factors that may significantly affect the osteoinductive properties of DBM and osteogenin. Soft-tissue collapse into the wound bed may likewise inhibit the proper migration of osteocompetent stem cells into the wound bed. Moreover, DBM in powder form is difficult to use.

Purified BMPs have osteoinductive effects in animals when delivered by a variety of means including fibrin glue (Hattori, T., *Nippon. Seikeigeka. Gakkai. Zasshi.* 64:824–834 (1990); Kawamura et al., *Clin. Orthop. Rel. Res.* 235:302–310 (1988); Schlag et al., *Clin. Orthop. Rel. Res.* 227:269–285 (1988) and Schwarz et al., *Clin. Orthop. Rel. Res.* 238:282–287 (1989)) and whole blood clots (Wang et al., *J. Cell. Biochem.* 15F:Q20 Abstract (1990)). However, Schwarz et al. (supra.) demonstrated neither a clear positive or negative effect of a matrix on ectopic osteoinduction or BMP-dependent osteoregeneration. Kawamura et al. (supra.) found a synergistic effect when partially purified BMP in a biomatrix was tested in an ectopic non-bony site. Consequently, the prior art presents an inconsistent and confusing picture of the applicability of delivery of an osteogenic supplement to a patient from a tissue sealant.

d. Vascular Prostheses

Artificial vascular prostheses, frequently made of dacron or polytetrafluoroethylene (PTFE), are used to replace diseased blood vessels in humans and other animals. To maximize patency rates and minimize the thrombogenicity of vascular prostheses, various techniques have been used including seeding of nonautologous endothelial cells onto the prothesis. Various substrates which adhere both to the vascular graft and endothelial cells have been investigated as an intermediate substrate to increase endothelial cell seeding. However, the use of nonautologous cells for the seeding the surface of the substrate raises the possibility of tissue rejection. See e.g., Schrenk et al., *Thorac. Cardiovasc. Surg.* 35:6–10 (1986). In addition, a confluent endothelium usually requires months to established, if it can be established at all. The delay results in a high rate of failure due to occlusion of the vascular prosthesis (see, e.g., Zilla et al., *Surgery* 105.515–522 (1989). This problem has been overcome by the chitin hydrogel of the present invention.

e. Angiogenesis

Angiogenesis is the induction of new blood vessels. Certain growth factors such as HBGF-1 and HBGF-2 are angiogenic. However, their in vivo administration when attached to: collagen sponges (Thompson et al., *Science* 241:1349–1352 (1988)); beads (Hayek et al., *Biochem. Biophys. Res. Commun.* 147:876–880 (1987)); solid PTFE fibers coated with collagen arranged in a sponge-like structure (Thompson et al., *Proc. Natl. Acad. Sci. USA* 86:7928–7932 (1989)); or by infusion (Puumala et al., *Brain Res.* 534:283–286 (1990)) resulted in the generation of random, disorganized blood vessels. Until the discovery of the present invention, these growth factors had not been used successfully to direct the growth of new blood vessels at a given site in vivo.

f. Site-Directed, Localized Drug Delivery

An efficacious, site-directed, drug delivery system is greatly needed in several areas of medicine. For example, localized drug delivery is needed in the treatment of local infections, such as in periodontitis, where the systemic administration of antimicrobial agents is ineffective. The problem after systemic administration usually lies in the low concentration of the antimicrobial agent which can be achieved at the target site. To raise the local concentration a systemic dose increase may be effective, but it also may produce toxicity, microbial resistance and drug incompatibility.

To circumvent some of these problems, several alternative methods have been devised, but none are ideal. For example, collagen and/or fibrinogen dispersed in an aqueous medium as an amorphous flowable mass, and a proteinaceous matrix composition which is capable of stable placement, have also been shown to locally deliver drugs (Luck et al., U.S. Reissue Pat. No. 33,375; Luck et al., U.S. Pat. No. 4,978, 332). Fibrin sealant have been used to deliver a variety of antibiotics, but only at relatively low concentrations and for relatively short periods of time ranging from a few hours to a few days (Kram et al., *J. Surg. Res.* 50:175–178 (1991)). Most of the antibiotics have been in freely water soluble forms and have been added during the preparation of the tissue sealant. However, their delivery is hampered by the limitations of the fibrin delivery system, which are overcome by the chitin hydrogel of the present invention.

The incorporation of tetracycline hydrochloride tetracycline hydrochloride (TET HCl) and other freely water soluble forms of antibiotic has often interfered with polymerization during the formation of an antibiotic-supplemented fibrin matrix (Schlag et al., *Biomaterials* 4:29–32 (1983)). Thus, the amount and concentration of the TET HCl that could be formulated with the hydrogel may be antibiotic-concentration dependent.

g. Controlled Drug Release

For some clinical applications controlled, localized drug release is desirable. Although, some drugs, especially antibiotics, have been incorporated into and been released from biomatrices, little or no control over the duration of the drug release has been possible. This is, at least partially, a reflection of the relatively short life of the drug-supplemented biomatrix. Therefore, there remains a long-felt need in the art to provide a means for extended, localized drug release, as are new techniques for the incorporation and extended release of other supplements from a biocompatible delivery system. This need is satisfied by the chitin hydrogel of the present invention.

Local implantation of antibiotics in a matrix has become popular in the treatment of wounds, such as open fractures or acute and chronic osteomyelitis. Several substances have been employed as the delivery vehicle, with polymethylmethacrylate (PMMA) being the most commonly utilized vehicle (Buchholz, H. W. et al., *J. Bone Joint Surgery (British)* 63:342–353 (1981); Buchholz, H. W. et al., *Clin. Orthop.* 190:96–108 (1984); Christian, E. P. et al., *J. Bone Joint Surg.* (*American*) 71:994–1004 (1989); Majid, S. A. et al., *Acta Orthop. Scand.* 56:265–268 (1985)). PMMA-antibiotic, which is surgically implanted after debriment of wound, is capable of significantly increasing local tissue levels of antibiotics while decreasing dead space. However, the major disadvantage of PMMA therapy is it is non-resorbable. If left in the wound after the antibiotic has eluted, it can act as a foreign body and additional surgery is required for its removal.

For example, acute osteomyelitis is a rapidly progressing infection of bone whereas the chronic form of osteomyelitis results from a long-standing infection of the bone (Waldvogel, F A, "Acute Osteomyelitis," In: *Orthopaedic Infection*, ed. by D. Schlossberg, New York, Springer-Verlag, 1988, p1–8). Acute osteomyelitis can be successfully treated with antibiotics provided the disease is diagnosed early, while for the chronic form, successful treatment requires debriment of the wound and administration of antibiotics. Antibiotics, an adjunct to thorough debridement, usually are administered systemically. However, conventional antibiotic systemic therapy results in the release of a therapeutically ineffective levels of antibiotics at the site of infection (Dash, A. and Suryanarayanan, R., *Pharmaceut. Res.* 9:993–1002 (1992)). Systemic treatment can also result in serious toxicity. Furthermore, the cost of large amounts of antibiotics used for systemic treatment may restrict therapy.

One solution to overcome the negative effects of systemic antibiotic therapy for osteomyelitis is local antibiotic delivery. Local antibiotic delivery can reduce systemic side effects by using a fraction of the systemic antibiotic dose to combat the infection. Local deposition of antibiotics has become increasingly popular in the treatment of osteomyelitis (Waldvogel (1988), supra), and several substances have been used as antibiotic delivery vehicles, however, none provide the advantages of the chitin hydrogel of the present invention.

h. The Disclosed Preparations Provide Life-Saving Emergency Treatment for Trauma Wounds Despite continued advances in trauma care, a significant percentage of the population, both military and civilian, suffer fatal or severe hemorrhage every year. An alarming number of fatalities are preventable since the occur in the presence of those who could achieve life-saving control of their wounds given adequate tools and training. The availability of the herein-disclosed chitin hydrogel satisfies the long-felt need for a advanced, easy-to-use, field-ready delivery system which can be effectively combined with the advantages of a hemostatic preparation.

The disclosed technology would also be available for the treatment of massed casualties in disaster situation, when the availability of the easy-to-use, self-contained hydrogel preparations disclosed below will permit local medical personnel and disaster relief workers to provide the injured with temporary treatment until definitive care becomes available. Moreover, the disclosed chitin hydrogel preparations will permit self-treatment in disaster victims, until medical assistance can be provided.

SUMMARY OF THE INVENTION

In one embodiment, this invention provides a composition of matter, comprising a chitin hydrogel or chitin-derived hydrogel, wherein the hydrogel does not inhibit full-thickness skin wound healing.

In another embodiment, this invention provides a composition of matter comprising a supplemented hydrogel comprising at least one growth factor.

In another embodiment, this invention provides a composition of matter comprising a supplemented hydrogel comprising at least one growth factor and/or a drug.

In another embodiment, this invention provides a composition of matter that promotes the directed migration of animal cells, comprising: a hydrogel; and an effective concentration of at least one growth factor, wherein the concentration of the growth factor is effective in promoting the directed migration of the animal cells.

In another embodiment, the present invention provides a composition of matter that promotes wound healing, comprising: a hydrogel; and an effective concentration of at least one growth factor, wherein the concentration is effective in promoting wound healing.

In another embodiment, the present invention provides a composition of matter that promotes the endothelialization of a vascular prosthesis, comprising: a hydrogel; and an effective concentration of at least one growth factor, wherein the concentration is effective in promoting the endothelialization of a vascular prosthesis.

In another embodiment, the present invention provides a composition of matter that promotes the proliferation and/or differentiation of animal cells, comprising: a hydrogel; and an effective concentration of at least one growth factor, wherein the concentration is effective in promoting proliferation and/or differentiation of animal cells.

In another embodiment, the present invention provides a composition of matter that promotes the localized delivery of at least one drug.

In another embodiment, the present invention provides a composition of matter that promotes the localized delivery of at least one growth factor.

In another embodiment, the present invention provides a process for promoting the healing of wounds, comprising applying to the wound, a composition that contains a supplemented hydrogel and an effective concentration of at least one growth factor, wherein the concentration is effective to promote wound healing.

In another embodiment, the present invention provides a process for promoting the endothelialization of a vascular prosthesis, comprising applying to the vascular prosthesis a composition that contains a chitin hydrogel and an effective concentration of at least one growth factor, wherein the concentration is effective to promote the endothelialization of a vascular prothesis.

In another embodiment, the present invention provides a process for promoting the proliferation and/or differentiation of animal cells, comprising placing the cells in sufficient proximity to a chitin hydrogel which contains an effective concentration of at least one growth factor, wherein the concentration is effective in promoting the proliferation and/or differentiation of the cells.

In a further embodiment, the present invention provides a process for the localized delivery of at least one drug to a tissue, comprising applying to the tissue a chitin hydrogel which contains at least one drug.

In another embodiment, the present invention provides a process for the localized delivery of at least one growth factor to a tissue, comprising applying to the tissue a chitin hydrogel which contains at least one growth factor.

In another embodiment, this invention provides a process for producing the directed migration of animal cells, comprising: placing in sufficient proximity to the cells, a chitin hydrogel which contains an effective concentration of at least one growth factor, wherein the concentration is effective to produce the desired directed migration of said cells.

In another embodiment, this invention provides a simple to use, fast acting, field-ready bandage for applying a hydrogel to wounded tissue in a patient, comprising an occlusive backing, affixed to which is a layer of dry materials comprising an effective amount of dry, purified chitin or chitosan to produce a tissue-sealing hydrogel matrix upon hydration. Further embodiments pertain to the use and preparation of the chitin bandage.

In yet another embodiment, this invention provides a simple to use, fast acting, field-ready dressing for treating wounded tissue in a patient, is formulated as an expandable foam comprising an effective amount of purified chitin or chitosan to produce a tissue-sealing hydrogel matrix upon hydration. Further embodiments pertain to the use and preparation of the chitin dressing.

In another embodiment, this invention provides a mixture of chitin hydrogel, DBM and/or purified BMP's. This mixture provides a matrix that allows the cellular components of the body to migrate into it and thus produce osteoinduction where needed. The matrix composition, enzymes (such as thrombin and plasmin), BMPs, growth factors and DBM and their concentrations are adequately formulated to optimize the longevity of this temporal scaffolding structure and the osteoinduction which needs to occur. All of the chitin hydrogel components are biodegradable, but during osteogenesis the mixture provides a non-collapsible scaffold that can determine the shape and location of the newly formed bone. Soft tissue collapse into the bony nonunion defect, which is a problem in bone reconstructive surgery, will thus be avoided. The use of hydrogel supplemented with growth factors such as CIF-A and CIF-B, infra, which promote cartilage development, will be useful in the reconstruction of lost, damaged or missing cartilage and/or bone.

In a preferred embodiment, an effective concentration of HBGF-1 is added to a chitin preparation to provide a growth factor-supplemented chitin hydrogel that possesses the ability to promote wound healing. In another preferred embodiment, an effective amount of a platelet-derived extract is added to the chitin hydrogel.

In other preferred embodiments, an effective concentration of a mixture of at least two growth factors are added to the chitin hydrogel and an effective amount of the growth factor-supplemented hydrogel is applied to the wounded tissue.

In addition to growth factors, drugs, polyclonal and monoclonal antibodies, oligonucleotides and other compounds, including, but not limited to, DBM, BMPs, osteogenic or cartilage inducing compositions may be added to the hydrogel. They accelerate wound healing, combat infection, neoplasia, and/or other disease processes, mediate or enhance the activity of the growth factor in the hydrogel, and/or interfere with hydrogel components which inhibit the activities of the growth factor in the hydrogel. These drugs may include, but are not limited to: antimicrobial compositions, including antibiotics, such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, and the like; and antiparasitic agents, such as pentamidine, and the like. The drugs may further include anti-inflammatory agents, such as $\alpha$-1-anti-trypsin, $\alpha$-1-antichymotrypsin, and the like; cytokines and interferons, such as $\alpha$- or $\beta$- or $\gamma$-interferon, $\alpha$- or $\beta$-tumor necrosis factor, and the like, and interleukins.

In an additional preferred embodiment, an effective concentration of cytotoxin or cell proliferation inhibiting composition is delivered by the chitin hydrogel. An effective concentration at least one cytotoxin or cell proliferation inhibiting composition is added to the chitin hydrogel.

In another embodiment, genetically altered cells and/or other cells may also be included in the hydrogels of this invention.

In additional embodiments, anything which does not destroy the matrix or the supplementary components added thereto can be added to the hydrogels of this invention.

In another embodiment, the supplemented hydrogel can be used in organoids and could contain, for example, growth factors such as FGF-1, FGF-2, FGF-4 and OP-1, or any recognized growth factor, including those listed above.

In another embodiment, this invention provides a composition that promotes the localized delivery of a poorly water soluble form of an antibiotic, such as the free base form of TET, and/or other drug.

In another embodiment, the present invention provides a method for cross-linking a chitin hydrogel.

In another embodiment, the present invention provides a system for the delivery of a supplement from a chitin hydrogel.

In another embodiment, the present invention provides a composition of matter for subcutaneous delivery that promotes the controlled, extended release of proteins for absorption into the blood stream.

In another embodiment, the present invention provides a composition of matter that promotes the delivery of coagulation proteins or factors or anticoagulant proteins or factors.

In another embodiment, the present invention provides a composition of matter that promotes the delivery of plasma proteins, comprising applying or injecting by subcutaneous, intradermal, intermuscular, intraperitoneal or intravenous injection a chitin hydrogel which contains at least one plasma protein, whereupon the concentration is effective to achieve therapeutic levels in situ or in the blood stream in individuals who have congenital or acquired deficiencies or defects of the protein.

In another embodiment, the present invention provides a composition of matter that promotes the delivery of Factor IX, comprising injecting or applying by subcutaneous, intradermal, intramuscular, intraperitoneal or intravenous injection of a chitin hydrogel which contains Factor IX, whereupon the concentration is effective to achieve therapeutic levels in the blood plasma in individuals with Hemophilia B.

In another embodiment, the present invention provides a composition of matter that promotes the delivery of Factor VIII, comprising injecting or applying by subcutaneous, intradermal, intramuscular, intraperitoneal or intravenous injection a chitin hydrogel which contains Factor VIII, whereupon the concentration is effective to achieve therapeutic levels in the blood plasma in individuals with Hemophilia A.

The present invention has several advantages over previously used compositions and methods. The first advantage is that the growth factor- and/or drug-supplemented chitin hydrogels of the present invention have many of the characteristics of an ideal biodegradable carrier, namely: they can be formulated to be free of non-mammalian proteins, thus eliminating or minimizing immunogenicity problems and foreign-body reactions; their administration is versatile; and their removal from the host's tissues is not required because the matrices are degraded by the host's own natural lytic system.

A second advantage is that the present invention provides a good way to effectively deliver growth factors, analgesics, antimicrobial compositions, anti-inflammatory compounds, antibodies, anticoagulants, antiproliferatives, cytokines, cytotoxins, chemotherapeutic drugs, interferons, hormones, hydroxyapatite, lipids, oligonucleotides, osteoinducers, polymers, polysaccharides, proteoglycans, polypeptides, protease inhibitors, proteins (including plasma proteins), steroids, vasoconstrictors, vasodilators, vitamins, minerals, stabilizers and the like, for a prolonged period of time to an internal or external wound. This is particularly advantageous since it appears that some growth factor receptors must be occupied for at least 12 hours to produce a maximal biological effect. Previously, there was no way to do this. The present invention allows for prolonged contact between the growth factor and its receptors to occur, and thus allows for the production of strong biological effects.

A third advantage of the present invention is that animal cells can migrate into and through, and grow in the chitin hydrogel of the present invention. This aids engraftment of the cells to neighboring tissues and prostheses, which cannot be achieved using commercially available European tissue sealants.

A fourth advantage is that because of its initial liquid nature, the hydrogel of the present invention can cover surfaces more thoroughly and completely than many previously available delivery systems. This is especially important for the use of the present invention in coating biomaterials and in promoting the endothelialization of a biomaterial, such as a vascular prostheses. The supplemented hydrogel will not only coat the interior and exterior of the vascular prosthesis, but also fill the pores contained therein, permitting the actual induction of migrating cells into the biomaterial. As a result, engraftment of autologous endothelial cells will occur along the whole length of the vascular prosthesis, thereby decreasing its thrombogenicity and antigenicity. Previously, engraftment started at the ends of the vascular prosthesis and proceeded, if at all, toward the interior of the same. To date, total engraftment of a biomaterial into a human is uncommon, primarily because delays allow thrombogenicity and antigenicity to develop. Moreover, previously used vascular prostheses have been primarily seeded with nonautologous cells, enhancing the possibility of rejection by the body. The cells were easily washed off by the shearing force of blood passing through a vascular prosthesis.

A fifth advantage is that the supplemented hydrogels of the present invention can be molded and thus can be custom made into almost any desired shape. For example, the chitin hydrogel can be supplemented with BMPs and/or DBM and can be custom made into the needed shape to most appropriately treat a bone wound. This cannot be done with DBM powder alone, because DBM powder will not maintain its shape. Moreover, the supplemented chitin hydrogel can be readily dried into thin sheets.

A sixth advantage is that the antibiotic-supplemented hydrogel of this invention, such as with TET, has been found to unexpectedly increased the longevity and stability of the chitin hydrogen, as compared to that of the unsupplemented hydrogel. This increased stability continues even after appreciable quantities of the antibiotic no longer remain in the matrix. For example, soaking a newly formed hydrogel in a saturated solution of TET produced from free base TET, or in a solution of CIP HCl, produces a matrix which is stable and preserved even after substantially all the TET or CIP has dissipated. As a result, one can expect an increased storage shelf life of the hydrogel, and possibly an increased persistence in vivo.

The seventh advantage of the present invention is a direct result of the prolonged longevity and stability of the chitin hydrogel. As a result of this unexpected increase in stability of the matrix, antibiotic or antiproliferative-supplemented hydrogel can be used to produce localized, long term delivery of a drug and/or a growth factor, and the like. This delivery will continue even after the stabilizing drug, such as TET or CIP, has substantially left the matrix. Inclusion of a solid form, preferably a poorly water soluble form of a drug, such as in free base form, into a matrix that has been stabilized by, for example, TET or CIP, permitting site-specific delivery of the supplement for an extended period of time. Some forms of drugs, such as free base TET, advantageously allow for both stabilization of the matrix and prolonged drug delivery, while other drugs may do one or the other, but not both. Such applications are not previously known in the art.

An eighth advantage of the present invention is that it allows site-directed angiogenesis to occur in vivo. While others have demonstrated localized non-specific angiogenesis, no one else has used a chitin hydrogel to promote site-directed angiogenesis.

A ninth advantage of the present invention is that because the components of the chitin hydrogel can be formulated into several forms of simple to use, fast-acting field dressings, it is now possible to control bleeding from hemorrhaging trauma wounds, thereby saving numerous lives that previously would have been lost. Although life-saving methods of treating such wounds are possible by trained medical personal or in fully-equipped clinics and hospitals, the present invention satisfies society's long-felt need for an easy-to-use, first-aid (or even self-applied) treatment that will, in emergency or disaster situations, allow an untrained individual to treat traumatic injuries to control hemorrhage until medical assistance is available.

A tenth advantage of the present invention is that, because the components of the chitin hydrogel can be formulated so as to release proteins and polypeptides at controlled rates for extended times, it is now possible to deliver proteins into peripheral sites by subcutaneous, intradermal, intramuscular, intraperitoneal or intravenous injection, in chitin hydrogel formulations which will release the protein at a rate suitable for absorption of the protein into the blood plasma at therapeutic and/or prophylactic levels.

DESCRIPTION OF THE PREFERRED EMBODIMENTS

Definitions

Figure 1:
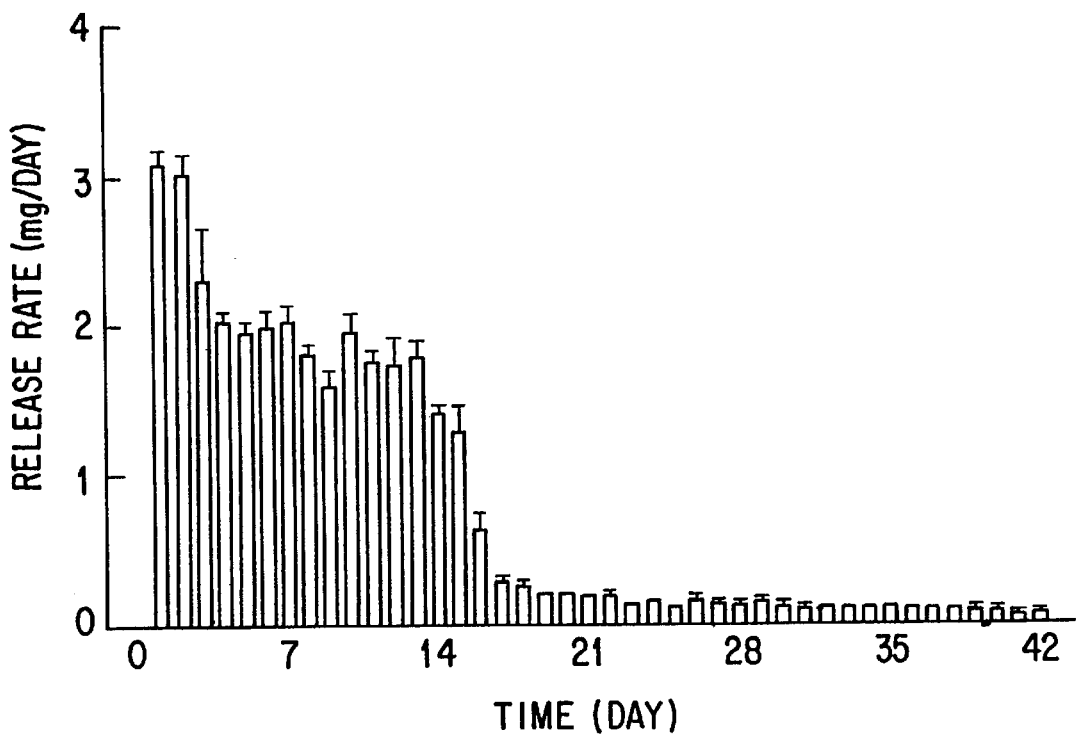
FIG. 1. Tetracycline release from NOC-chitosan matrices under limited sink conditions. The concentration of NOC-chitosan was 66 mg/ml and the amount of tetracycline in each disk was 50 mg. Error bars represent the standard deviation for n=5.

Unless defined otherwise, all technical and scientific terms used herein have the same meaning as is commonly understood by one of skill in the art to which this invention belongs. All patents and publications mentioned herein are incorporated by reference.

A "polysaccharide" as used herein, refers to a compound comprised of hundreds or even thousands of monosaccharide units/molecule. These units are held together by glycoside linkages.

"Chitin" as used herein, is a polysaccharide composition prepared from the shells of arthropods, particularly crustacean or insects, which is broadly used to include chemical derivatives of the polysaccharide, further including cross-linked derivatives. The term is particularly meant to include all soluble chitin derivatives and all carboxymethyl chitosans, wherein "chitosan" is meant to include any polysaccharide produced by hydrolysis of acetamido groups of N-acetyl glucosan in chitin. Further encompassed is NOC-chitosan, a water soluble chitin derivative formed by carboxymethlyation of biomedical grade chitosan. U.S. Pat. No. 4,619,995 to Hayes, herein incorporated by reference, sets forth the composition and preparation of NOC-chitosan. The polysaccharide or its derivatives can be prepared in powder or solid form from freeze- or air-dried chitin, or from ground chitin as originally produced.

A "cross-linked chitin hydrogel" of the type used in the bandage or in the wound dressing of the present invention, refers to a hydrogel wherein the chitin component is cross-linked to form a stable matrix by the addition of a cross-linking agent. Such agents may include, but are not limited to, glyoxal, gluteraldehyde, PEG succinamide, PEG succimidyl succinate or PEG succimidyl propionate, wherein, however, the particular cross-linking agent selected is not critical to the specific embodiment.

A "hydrogel" as used herein, refers to a semisolid composition constituting a substantial amount of water, and in which polymers or mixtures thereof are dissolved or dispersed.

The term "supplemented" as used herein, refers to any addition of a supplementary composition or compound, or any combination thereof to the chitin hydrogen. The addition may be made during the preparation or hydration of the chitin hydrogel. It may be mixed with the chitin components in dry, liquid or gelled form prior to hydration, or it may be added to the hydrogel as the matrix sets-up after hydration, or it may be added, as in by soaking, after the hydrogel has been prepared. Alternately, any one of the supplements may be supplied to the hydrogel by the hydrating agent. Furthermore, the supplement may be added by any combination of the above describe addition mechanisms.

The term "hydrating agent" as used herein, is meant to broadly refer to any physiologically acceptable hydrating liquid or gel that can sufficiently hydrate the chitin components to form a hydrogel. Exemplary hydrating agents may include water, saline, buffers, and the like.

A "supplemented chitin hydrogel" as used herein, includes any hydrogel prepared from chitin or any chemical, enzymatic or biological derivative thereof that, without substantial modification, can serve as a carrier vehicle for the delivery of one or more analgesics, antimicrobial compositions, anti-inflammatory compounds, antibodies, anticoagulants, antiproliferatives, cytokines, cytotoxins, chemotherapeutic drugs, growth factors, interferons, hormones, hydroxyapatite, lipids, oligonucleotides, osteoinducers, polymers, polysaccharides, proteoglycans, polypeptides, protease inhibitors, proteins (including plasma proteins), steroids, vasoconstrictors, vasodilators, vitamins, minerals, stabilizers, and the like, or mixtures thereof, and that, by virtue of its physical matrix, chemical characteristics and/or adsorptive properties, can maintain contact with the site for a time sufficient for the supplemented to deliver an effective amount of the supplement to produce its desired effect, for example to promote wound healing.

A "matrix" as used herein, refers to the structural properties or architecture of a solid or semi-solid (including a hydrogel) in which other components may be cast, mixed, dispersed or dissolved.

A "plasma protein" as used herein, refers to any protein found within the plasma of a patient, or which is found in the plasma of a normal individual or animal, but which is absent or deficient in the patient (e.g, hemophilias). Particularly relevant to the present invention are plasma protein members of the blood clotting cascade, including those clotting factors which are thrombin sensitive; that is, those blood clotting factor molecules which have been shown to include one or more binding sites for thrombin. Included within this term, however, are the following: albumin; immunoglobulins, including immunoglobulin A, M and G; fibrinogen; coagulation factors, including Factors II, VII, VIII, IX, X and XIII; plasminogen; protein C; protein S; plasma proteinase inhibitors, including antithrombin III, α1-antitrypsin, α2-macroglobulin, and C1 esterase inhibitor; α1-acid glycoprotein; ceruloplasmin; haptoglobin; transferrin; complement components C1 through C9; C4b binding protein; interalpha-trypsin inhibitor; apolipoproteins, including A-1, A-11, B, C and E; fibronectin and angiostatin; also including all coagulation proteins (e.g., Factors II, VII, VIIa, VIII, IX, X, XIII, protein C, and the like).

"Factor IX" (FIX) as used herein, refers to a plasma glycoprotein that plays a pivotal role in blood coagulation. A congenital X-linked deficiency of biologically active FIX results in hemophilia B (Christmas disease), a potentially life-threatening bleeding disorder.

The terms "localized" or "site-specific" are used interchangeably herein, to mean delivery of a supplement within a limited area, as opposed to a "systemic" delivery through the body of a patient. Systemic therapy often results in a therapeutically ineffective level of an antibiotic, drug or the like, at the site of interest (wound, infection and the like). Systemic treatment can also result in serious toxicity. Furthermore, the cost of large amounts of each supplement used for systemic treatment may restrict therapy. By comparison, localized delivery can reduce systemic side effects by using a fraction of the systemic antibiotic dose to combat the infection.

"Sustained release" or "long term release or delivery" are phrases used interchangeably herein, to mean longer than the expected delivery of a supplement from a chitin hydrogel matrix based solely upon diffusion kinetics. Typically, delivery will be at least a day or more, and may extend to weeks or months. The long term release can be achieved by any of a number of mechanisms. The supplement may be added to the chitin hydrogel as a solid. The supplement may be added in solution in a carrier or hydrting agent which has a higher rate of diffusion than that of the chitin hydrogel so that upon diffusion of the carrier or hydrating agent from the hydrogel, the supplement is precipitated within the matrix. Ethanol would be such a carrier. The supplement may be precipitated into the matrix from a supersaturated solution. The supplement may be added in such a mass as to exceed the volume which would be soluble in the hydrogel. The supplement may be added as an emulsion or dispersion, for example, in a lipid or oil-based carrier. Release of the supplement from the hydrogel may also be delayed because of specific physical or biochemical interactions with the chitin hydrogel matrix.

A "wound" as used herein, refers to any damage to any tissue in a living organism. The tissue may be an internal tissue, such as the stomach lining or a bone, or an external tissue, such as the skin. As such, a wound may include, but is not limited to, a gastrointestinal tract ulcer, a broken bone, a neoplasia, and cut or abraded skin. A wound may be in a soft tissue, such as the spleen, or in a hard tissue, such as bone. The wound may have been caused by any agent, including traumatic injury, infection or surgical intervention.

A "biomaterial" as used herein, refers to any physiologically useful material which can be coated or infused with the chitin hydrogel and placed into the body of a patient, or further coated with additional material including viable cells before being placed into the patient. The biomaterial may be formed, for example, into vascular grafts, orthopedic devices, such as hip or joint replacements, catheters, indwelling shunts and implants, bone or cartilage replacements, dental or periodontal tissue replacements, contact lens, an artificial covering for burned tissue, and the like.

A "growth factor-supplemented chitin hydrogel" as used herein, is a hydrogel prepared from chitin, or any chemical, enzymatic or biological derivative thereof, to which at least one growth factor has been added at a concentration that is effective for its stated purpose. The growth factor can, for example, accelerate, promote or improve wound healing, or tissue (re)generation. The growth factor-supplemented chitin hydrogel may also contain additional components, including drugs, antibodies, anticoagulants and other compounds that: 1) potentiate, stimulate or mediate the biological activity of a growth factor in the chitin hydrogel; 2) decrease the activities of components of the growth factor-supplemented chitin hydrogel which would inhibit or destroy the biological activities of a growth factor in the hydrogel; 3) allow prolonged delivery of the supplement from the chitin hydrogel; or 4) possess other desirable properties.

A "potentiating compound" as used herein, is a regulatory compound that mediates or otherwise increases the biological activity of a growth factor in the chitin hydrogel. Heparin is an example of a compound that potentiates the biological activity of HBGF-1.

An "inhibiting compound" as used herein, is a regulatory compound that inhibits, interferes with, or otherwise destroys a deleterious activity of a component of the chitin hydrogel that would interfere with or inhibit the biological activity of a growth factor or factors in the chitin hydrogel. Inhibiting compounds may exert their effect by protecting the growth factor from degradation. An inhibiting compound does not, however, inhibit any activities that are essential for the desired properties, such as, for example, wound healing of the growth factor-supplemented chitin hydrogel. An example of an inhibiting compound is heparin. Thus, it is clear that in certain circumstances, the same regulatory compound may be, at the same time, a promoter compound for the supplementary growth factor and an inhibitor of factors which would otherwise have a deleterious effect on the desired activity of the growth factor.

A "growth factor" as used herein, includes any soluble factor that regulates or mediates cell proliferation, cell differentiation, tissue regeneration, cell attraction, wound repair and/or any developmental or proliferative process. The growth factor may be produced by any appropriate means including extraction from natural sources, production through synthetic chemistry, production through the use of recombinant DNA techniques and any other techniques, including virally inactivated, growth factor(s)-rich platelet releasate, which are known to those of skill in the art. The term growth factor is meant to include any precursors, mutants, derivatives, or other forms thereof which possess similar biological activity(ies), or a subset thereof, to those of the growth factor from which it is derived or otherwise related.

"HBGF-1," which is also known to those of skill in the art by alternative names, such as endothelial cell growth factor (ECGF) and FGF-1, as used herein, refers to any biologically active form of HBGF-1, including HBGF-1β, which is the precursor of HBGF-1α and other truncated forms, such as FGF. U.S. Pat. No. 4,868,113 to Jaye et al., herein incorporated by reference, sets forth the amino acid sequences of each form of HBGF. HBGF-1 thus includes any biologically active peptide, including precursors, truncated or other modified forms, or mutants thereof that exhibit the biological activities, or a subset thereof, of HBGF-1.

Other growth factors may also be known to those of skill in the art by alternative nomenclature. Accordingly, reference herein to a particular growth factor by one name also includes any other names by which the factor is known to those of skill in the art and also includes any biologically active derivatives or precursors, truncated mutant, or otherwise modified forms thereof.

"Biological activity" as used herein, refers to one or all of the activities that are associated with a particular growth factor in vivo and/or in vitro. Generally, a growth factor exhibits several activities, including mitogenic activity (the ability to induce or sustain cellular proliferation) and also non-mitogenic activities, including the ability to induce or sustain differentiation and/or development. In addition, growth factors are able to recruit or attract particular cells from which the proliferative and developmental processes proceed. For example, under appropriate conditions HBGF-1 can recruit endothelial cells and direct the formation of vessels therefrom. By virtue of this activity, growth factor-supplemented chitin hydrogel may thereby provide a means to enhance blood flow and nutrients to specific sites.

"Extended longevity" as used herein, means at least a two fold increase in the visually observable, useful in vitro lifespan of a chitin hydrogel.

"Demineralized bone matrix" (DBM) as used herein, means the organic matrix of bone that remains after bone is decalcified with hydrochloric or another acid.

"Bone morphogenetic proteins" (BMPs) as used herein, means a group of related proteins originally identified by their presence in bone-inductive extracts of DBM. At least 8 related members have been identified and are designated BMP-1 through BMP-8. The BMPs are also known by other names. BMP-2 is also known as BMP-2A. BMP4 is also known as BMP-2B. BMP-3 is also known as osteogenin. BMP-6 is also known as Vgr-1. BMP-7 is also known as OP-1. Thus, BMP is meant to include, but is not limited to BMP-1 through BMP-8.

"Augmentation" as used herein, means using a supplemented or unsupplemented chitin hydrogel to change the internal or external surface contour of a component of an animal's body.

A "damaged bone" as used herein, is a bone which is broken, fractured, missing a portion thereof, or otherwise not healthy, normal bone.

A "deficient bone" as used herein, is a bone which has an inadequate shape or volume to perform its function.

"Bone" or "DBM" as used herein, which is used to supplement a chitin hydrogel can be in the form of powder, suspension, strips or blocks or other forms as necessary to perform its desired function.

An "organoid" as used herein, means a structure that may be composed of natural, artificial, or a combination of natural and artificial elements, that wholly or in part, replaces the function of a natural organ. An example would be an artificial pancreas consisting of a network of capillaries surrounded by cells transfected with an expression vector containing the gene for insulin. Such an organoid would function to release insulin into the bloodstream of a patient with Type I diabetes.

In the embodiments of this invention, the hydrogel may be chitin, chitosan, or any hydrogel-forming derivative of chitin. Varying the concentration of the chitin material and cross-linking material may affect the density of the final matrix and vary the setting times. While this effect is readily known, it is not generally appreciated that it may be used to maximize the effectiveness of the matrix as a delivery vehicle, when used alone or supplemented. Because of this effect one can alter the time between the mixing of the chitin components and the setting of the hydrogel. Thus, one can allow the hydrogel to, for example, flow freely into deep crevices in a wound, permitting it to fill the wound completely before the matrix sets. Alternatively, one can allow the chitin hydrogel to set quickly enough to prevent it from exiting the wound site, especially if the wound is leaking fluid under pressure (i.e., blood, lymph, intercellular fluid, etc). This property is also important to keep the hydrogel from clogging delivery devices with long passages, i.e., catheters, endoscopes, etc., which is important to allow the application of the chitin hydrogel or supplemented hydrogel to sites in the body that are only accessible by surgery. This effect is also important in keeping the insoluble supplements in suspension and preventing them from settling in the applicator or in the tissue site.

In the compositions of this invention containing a growth factor, the composition may contain an inhibiting compound and/or potentiating compound, wherein the inhibiting compound inhibit the activities of the hydrogel that interfere with any of the biological activities of the growth factor, the potentiating compound potentiate, mediate or enhance any of the biological activities of the growth factor, and wherein the concentration of the inhibiting and/or potentiating compound is effective for achieving the inhibition, potentiation, mediation or enhancement. Also applicable in this embodiment are regulatory compounds which simultaneously exhibit an inhibiting effect on exogenous factors, while at the same time potentiating, mediating or enhancing the effect of a growth factor contained within the matrix.

The growth factor-supplemented hydrogels of this invention are useful for promoting the healing of wounds, especially those that do not readily heal, such as skin ulcers in diabetic individuals, and for delivering growth factors including, but not limited to, angiogenins; endothelins; hepatocyte growth factor and keratinocyte growth factor; fibroblast growth factors, including fibroblast growth factor-1 (FGF-1), fibroblast growth factor-2 (FGF-2), and fibroblast growth factor-4 (FGF-4); platelet-derived growth factors (PDGF); insulin-binding growth factors (IGF), including insulin-binding growth factor-1 and insulin-binding growth factor-2; epidermal growth factor (EGF); transforming growth factors (TGF), including transforming growth factor-α and transforming growth factor-β; cartilage-inducing factors (CIF), including CIP-A and CIP-B; osteoid-inducing factor (OIF); osteogenin and other bone growth factors; bone morphogenetic growth factors (BMP), including BMP-1 and BMP-2; collagen growth factor; heparin-binding growth factors, including heparin-binding growth factor-1 and heparin-binding growth factor-2; cytokines; interferons; hormones and biologically active derivatives thereof, and providing a medium for prolonged contact between a wound site and the growth factor.

The growth factor-supplemented chitin hydrogel may be used to treat burns and other skin wounds and may comprise a hydrogel supplemented with one or more of the following: a growth factor, an antibiotic and/or an analgesic, etc. The growth factor-supplemented hydrogel may be used to aid in the engraftment of a natural or artificial graft, such as skin to a skin wound. They may also be used cosmetically, for example in hair transplants, where the hydrogel might contain FGF, EGF, antibiotics and minoxidil, as well as other compounds. An additional cosmetic use for the compositions of this invention is to treat wrinkles and scars instead of using silicone or other compounds to do so. In this embodiment, for example, the hydrogel may contain FGF-1, FGF-4, and/or PDGFs, and fat cells.

The growth factor-supplemented hydrogels may be applied to surgical wounds, broken bones or gastric ulcers and other such internal wounds in order to promote healing thereof. The hydrogels of this invention may be used to aid the integration of a graft, whether artificial or natural, into an animal's body as for example when the graft is composed of natural tissue. The hydrogels of this invention can be used to combat some of the major problems associated with certain conditions such as periodontitis, namely persistent infection, bone resorption, loss of ligaments and premature re-epithelialization of the dental pocket.

In addition to growth factors, drugs, polyclonal and monoclonal antibodies, oligonucleotides and other compounds, including, but not limited to, DBM, BMPs, osteogenic or cartilage inducing compositions may be added to the hydrogel. They accelerate wound healing, combat infection, neoplasia, and/or other disease processes, mediate or enhance the activity of the growth factor in the hydrogel, and/or interfere with hydrogel components which inhibit the activities of the growth factor in the hydrogel. These drugs may include, but are not limited to: antimicrobial compositions, including antibiotics, such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, and the like; and antiparasitic agents, such as pentamidine, and the like. The drugs may further include anti-inflammatory agents, such as $\alpha$-1-anti-trypsin, $\alpha$-1-antichymotrypsin, and the like; cytokines and interferons, such as $\alpha$- or $\beta$- or $\gamma$-interferon, $\alpha$- or $\beta$-tumor necrosis factor, and the like, and interleukins.

An effective concentration of cytotoxin or cell proliferation inhibiting composition may also be delivered by the chitin hydrogel. An effective concentration at least one cytotoxin or cell proliferation inhibiting composition is added to the chitin hydrogel, which upon delivery may act as an alkylating agent, enzyme inhibitor, proliferation inhibitor, lytic agent, DNA synthesis inhibitor, membrane permeability modifier, DNA intercalator, metabolite, mustard derivative, protein production inhibitor, ribosome inhibitor, inducer of apoptosis, angiogenesis inhibitor, neurotoxin, and the like. More specifically the cytotoxin or cell proliferation inhibiting composition delivered by the chitin hydrogel may include, for example, 5-fluorouracil (5-FU), taxol and/or taxotere, actinomycin D, adriamycin, azaribine, bleomycin, busulfan, butyric acid, carmustine, chlorambucil, cisplatin, cytarabine, cytarabine, dacarbazine, estrogen, hormone analogs, insulins, hydoxyurea, L-asparaginase, lomustine, melphalan, mercaptopurine, methotrexate, mitomycin C, prednisilone, prednisone, procarbazine, steroids, streptozotocin, testosterone, thioguanine, thiotepa, tributyrin, vinblastine, vincristine, gentamycin, carboplatin, cyclophosphamide, ifosphamide, maphosphamide, retinoic acid, ricin, diphtheria toxoid, venoms, antistatin or other plasminogen derivatives, and functionally equivalent analogs thereof; colony stimulating factors; erythropoietin;; steroids; anesthetics; analgesics; and hormones. The above-mentioned drugs may be used to treat, reverse or prevent neoplasias, cell hyperproliferation. Neurotoxins, including antibiotics having neurotoxic effects such as gentamycin, may also be used to treat specific disorders, such as Meneir's disease. One or more of the above-mentioned cytotoxins or cell proliferation inibiting compositions may be advantageously combined in the chitin hydrogel with any of above-referenced analgesics, antimicrobial compositions, anti-inflammatory compounds, antibodies, anticoagulants, antiproliferatives, cytokines, cytotoxins, chemotherapeutic drugs, growth factors, interferons, hormones, hydroxyapatite, lipids, oligonucleotides, osteoinducers, polymers, polysaccharides, proteoglycans, polypeptides, protease inhibitors, proteins (including plasma proteins), steroids, vasoconstrictors, vasodilators, vitamins, minerals, stabilizers, and the like.

Other compounds which may be added to the hydrogel include, but are not limited to: vitamins and other nutritional supplements; hormones; glycoproteins; fibronectin; peptides and proteins; carbohydrates (both simple and/or complex); proteoglycans; antiangiogenins; antigens; oligonucleotides (sense and/or antisense DNA and/or RNA); BMPs; DBM; osteogenic and cartilage inducing compositions; antibodies (for example, to infectious agents, tumors, drugs or hormones); and gene therapy reagents; anticoagulants; hormones; hydroxyapatite; lipids; polymers; polysaccharides; polypeptides; protease inhibitors; proteins (including plasma proteins), steroids, vasoconstrictors; vasodilators; minerals; stabilizers, and the like.

The studies reported herein, unexpectedly demonstrate that the inclusion of compounds such as the free base TET or ciprofloxacin HCl (CIP—HCl), in hydrogel or the treatment of hydrogel therewith confers extended longevity to the supplemented hydrogel. This phenomenon can be exploited to increase the duration of a drug's release from the hydrogel. Alternatively, this phenomenon can be exploited to modulate the release of drugs other than the compound used to stabilize the hydrogel, which is also incorporated into the TET-hydrogel, and/or to cause the matrix to persist for a greater period in vivo or in vitro.

In general, poorly water soluble forms of a drug, such as the free base of TET, increase the delivery of the drug from the hydrogel more than freely water soluble forms thereof. Therefore, the drug may be bound to an insoluble carrier, such as activated charcoal, within the hydrogel to prolong the delivery of the drug from the supplemented hydrogel.

Preparation of Supplemented Chitin Hydrogel

As a first step when practicing any of the embodiments of the invention disclosed herein, the supplement must be selected. The supplement may be prepared by methods known to those of skill in the art, may be purchased from a supplier thereof, or may be prepared according to the methods of this application. In a preferred embodiment, growth factor, drug-or DBM-supplemented chitin hydrogel is prepared.

In any of the embodiments of the present invention the supplement may be added to any of the components before they are mixed.

Preparation of Chitin Hydrogel

In certain embodiments of this invention such as, but not limited to, vascular prostheses, and bone and cartilage augmentation, a hydrogel which allows cells to migrate into and/or through it may preferably be used.

Any chitin or its derivative, such as a commercially available chitosan, may be used in some embodiments of this invention. For these uses, such as localized drug delivery, the particular composition of the selected chitin or derivative is not critical as long as it functions as desired. Commercially available chitin derivatives may be supplemented with growth factors, antibiotics and/or other drugs for use in the embodiments of this invention including, but not limited to: cellular proliferation and/or differentiation; drug delivery; growth factor delivery; tissue generation or regeneration; endothelialization of a vascular graft or shunt; and the like.

In a preferred embodiment of this invention, the total polysaccharide concentration in the hydrogel is from about 1 to 120 mg/ml. In a more preferred embodiment, the total polysaccharide concentration in the hydrogel is from about 10 to 100 mg/ml. In the most preferred embodiment, the total polysaccharide concentration in the prepared chitosan is from about 20 to 80 mg/ml.

In preparing the chitosan, sterile water for injection or a pharmacologically acceptable buffer, such as PBS, or hydrating agent should be used.

Although the concentration(s) of growth factor(s), drugs and other compounds will vary depending on the desired objective, the concentrations must be great enough to allow them to be effective to accomplish their stated purpose. In a preferred embodiment of this invention, the growth factor concentration is from about 1 ng/ml to 1 mg/ml of chitin hydrogel. In a more preferred embodiment, the growth factor concentration is from about 1 μg/ml to 100 μg/ml of chitin hydrogel. In the most preferred embodiment, the growth factor concentration is from about 5 μg/ml to 20 μg/ml of chitin hydrogel. In a preferred embodiment of this invention the TET or CIP concentration is from 0.01 to 350 mg/ml chitin hydrogel. In a more preferred embodiment of this invention the TET or CIP concentration is 0.01–200 mg/ml. In the most preferred embodiment of this invention the TET or CIP concentration is 1–150 mg/ml. The amount of the supplements to be added can be empirically determined by one of skill in the art by testing various concentrations and selecting that which is effective for the intended purpose and the site of application.

Preparation of Growth Factors

The growth factor, or mixtures thereof, may be prepared by any method known to those of skill in the art or may be purchased commercially. Any growth factor may be selected including, but not limited to, for example, growth factors that stimulate the proliferation and/or attraction of certain cell types, such as endothelial cells, fibroblasts, epithelial cells, smooth muscle cells, hepatocytes, and keratinocytes, and/or growth factors which inhibit the growth of the same cell types and smooth muscle cells. Such selection may be dependent upon the particular tissue site for which the growth factor-supplemented chitin hydrogel will be applied and/or the type of effect desired. For example, an EGF-supplemented chitin hydrogel may be preferred for application to wounds in the eye and for treating gastric ulcers while an osteogenin-supplemented chitin hydrogel may be preferred for application to bone fractures and bone breaks in order to promote healing thereof.

In another preferred embodiment HBGF-1β was prepared and added to chitin hydrogel. HBGF-1β, or HBGF-1α, or any other active form of HBGF-1, can be purified from natural sources, from genetically engineered cells that express HBGF-1 or a derivative thereof, or by any method known to those of skill in the art.

HBGF-1β has been prepared using recombinant DNA methodology (Jaye et al., U.S. Pat. No. 4,868,113; Jaye et al., *J. Biol. Chem.* 262:16612–16617 (1987)).

In addition to HBGF-1, other growth factors that may be added to the chitin hydrogel include, but are not limited to, HBGF-2, IGF-1, EGF, TGF-β, TGF-α, any platelet-derived growth factor or extract, BMPs, and mixtures of any growth factors. For example, platelet-derived extracts, which serve as rich sources of growth factors, may be added to the chitin hydrogel in addition to or in place of other growth factors, such as HBGF-1.

In a preferred embodiment, a platelet-derived extract, prepared by any method known to those of skill in the art, is added to a chitin hydrogel. Such an extract has been prepared from plasma derived platelets for use with chitin hydrogel. Platelet-derived wound healing factor (PDWHF) may be prepared and added to chitin hydrogel (Knighton et al., *Ann. Surg.* 204:322–330 (1986)).

Additional Components of Growth Factor-Supplemented Chitin Hydrogel

The chitin hydrogels contemplated for use with growth factors contain components, some of which may interfere with the biological activity of the selected growth factor. Therefore, it may be necessary to include additional compounds, such as protease or other inhibitors, that protect the selected growth factor from the action of other components in the chitin hydrogel which interfere with or destroy the biological activity of the growth factor.

Selection of the particular inhibiting compound may be empirically determined by using methods, discussed below, that assess the biological activity of the growth factor in the chitin hydrogel. Methods to assess biological activity are known to those of skill in the art.

In addition, in order for certain growth factors to exhibit their biological activities, it may be necessary to include compounds that potentiate or mediate the desired activity. For example, heparin potentiates the biological activity of HBGF-1 in vivo (see, e.g., Burgess et al., *Annu. Rev. Biochem.* 58:575–606 (1989)).

The supplemented chitin hydrogel of the present invention may contain compounds such as drugs, other chemicals, and proteins. These may include, but are not limited to: antibiotics such as TET, ciprofloxacin, amoxicillin, or metronidazole, anticoagulants, such as activated protein C, heparin, prostracyclin ($PGI_2$), prostaglandins, leukotrienes, antithrombin III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers; chemoattractants; local anesthetics such as bupivacaine; and antiproliferative/antitumor drugs such as 5-fluorouracil (5-FU), taxol and/or taxotere; neurotoxins and the like. These supplemental compounds may also include polyclonal, monoclonal or chimeric antibodies, or functional derivatives or fragments thereof. They may be antibodies which, for example, inhibit smooth muscle proliferation, such as antibodies to PDGF, and/or TGF-β, or the proliferation of other undesirable cell types within and about the area treated with the chitin hydrogel. These antibodies can also be useful in situations where anti-cancer, anti-platelet or anti-inflammatory activity is needed. In general, any antibody whose efficacy would be improved by site-directed delivery may benefit from being used with this chitin hydrogel delivery system.

Assays for Assessing the Wound Healing Properties of a Growth Factor-Supplemented Chitin Hydrogel In order to ascertain whether a particular growth factor-supplemented chitin hydrogel promotes wound healing and to select optimal concentrations of the growth factor to do the same, the composition may be tested by any means known to those of skill in the art (see, e.g., Tsuboi et al., *J. Exp. Med.* 172:245–251 (1990); Ksander et al., *J. Am. Acad. Dermatol.* 22:781–791 (1990); and Greenhalgh et al., *Am. J. Path.* 136:1235 (1990)). Any method including both in vivo and in vitro assays, by which the activity of the selected growth factor in the chitin hydrogel composition can be assessed may be used. For example, the activity of HBGF-1β may be assessed using two independent in vitro assays. In the first, the proliferation of endothelial cells that had been suspended in a shallow fluid layer covering a plastic surface which had been impregnated with growth factor-supplemented chitin hydrogel is measured. In the second, the incorporation of $^3$H-thymidine in cultured fibroblasts in the presence of HBGF-1 is measured. In an in vivo assay, a chitin hydrogel supplemented with HBGF-1β is tested for its ability to promote healing in vivo using mice as a model system.

The ability of the growth factor-supplemented chitin hydrogel to induce cell proliferation and to recruit cells may also be assessed by in vitro methods known to those of skill in the art. For example, the in vitro assays, described above for measuring the biological activity of growth factors, may be used to test the activity of the growth factor in the chitin hydrogel composition. In addition, the effects of adding inhibiting and/or potentiating compounds can also be assessed.

Generally, the necessity for adding inhibiting and/or potentiating compounds can be empirically determined. Heparin, which is known to bind to HBGF-1 and protect it from certain proteolytic activities, was added to the HBGF-1-supplemented chitin hydrogel. The addition of relatively low concentrations of heparin protected HBGF- 1β from cleavage that would destroy its biological activity in the chitin hydrogel. Therefore, chitin hydrogel compositions that include HBGF-1 may include heparin or some other substance that inhibits the cleavage of HBGF-1 by thrombin or other proteolytic components of the chitin hydrogel.

Similarly, the ability of a selected inhibitor to protect a growth factor from degradation by chitin hydrogel components may be assessed by any method known to those of skill in the art.

It can also be empirically determined whether a particular compound can be used to potentiate, mediate or enhance the biological activity of a growth factor in chitin hydrogel.

Topical or Internal Application of the Growth Factor-Supplemented Chitin Hydrogel to an Internal or External Wound Prior to clinical use, the growth factor and chitin hydrogel, or the growth factor-supplemented chitin hydrogel is pasteurized or otherwise treated to inactivate any pathogenic contaminants therein, such as viruses. Methods for inactivating contaminants are well-known to those of skill in the art and include, but are not limited to, solvent-detergent treatment and heat treatment (see, e.g., Tabor et al., *Thrombosis Res.* 22:233–238 (1981) and Piszkiewicz et al., *Transfusion* 28:198–199 (1988)).

The supplemented chitin hydrogel is applied directly to the wound, other tissue or other desired location. Typically for external wounds it can be applied directly by any means, including spraying on top of the wound. It can also be applied internally, such as during a surgical procedure. When it is applied internally, such as to bones, the clot gradually dissolves over time.

Preparation of Antimicrobial Compositions

The antimicrobial composition, or mixtures thereof, used to supplement the chitin hydrogel, may be prepared by any method known to those of skill in the art or may be purchased commercially.

Preparation of Plasma Proteins

The plasma proteins, or mixtures thereof, used to supplement the chitin hydrogel, may be prepared by any method known to those of skill in the art or may be purchased commercially. In particular, such plasma proteins will include thrombin-sensitive blood clotting factors, such as Factor IX.

Preparation of Antibodies

The antibodies, or mixtures thereof, used to supplement the chitin hydrogel, may be prepared by any method known to those of skill in the art or may be purchased commercially.

Preparation of Cytotoxins or Cell Proliferation Inhibiting Compositions

The cytotoxins or cell proliferation inhibiting compositions, or mixtures thereof, used to supplement the chitin hydrogel, may be prepared by any method known to those of skill in the art or may be purchased commercially. The cytotoxin or cell proliferation inhibiting composition may act as an alkylating agent, enzyme inhibitor, proliferation inhibitor, lytic agent, DNA synthesis inhibitor, membrane permeability modifier, DNA intercalator, metabolite, mustard derivative, protein production inhibitor, ribosome inhibitor, inducer of apoptosis, angiogenesis inhibitor, neurotoxin, and the like. More specifically the cytotoxin or cell proliferation inhibiting composition delivered by the chitin hydrogel may include, for example, 5-fluorouracil (5-FU), taxol and/or taxotere, actinomycin D, adriamycin, azaribine, bleomycin, busulfan, butyric acid, carmustine, chlorambucil, cisplatin, cytarabine, cytarabine, dacarbazine, estrogen, hormone analogs, insulins, hydoxyurea, L-asparaginase, lomustine, melphalan, mercaptopurine, methotrexate, mitomycin C, prednisilone, prednisone, procarbazine, steroids, streptozotocin, testosterone, thioguanine, thiotepa, tributyrin, vinblastine, vincristine, gentamycin, carboplatin, cyclophosphamide, ifosphamide, maphosphamide, retinoic acid, ricin, diphtheria toxoid, venoms, antistatin or other plasminogen derivatives, and functionally equivalent analogs thereof.

Self-Contained Applications of the Supplemented Chitin Hydrogel for Internal or External Wounds The chitin hydrogel may be formulated as a self-contained wound dressing, or bandage. The self-contained dressing or bandage is easy-to-use, requiring no advanced technical knowledge or skill to operate. It can even be self-administered as an emergency first aid measure.

The self-contained chitin hydrogel-containing wound dressing or bandage is an advancement over the current technology in that the field-ready preparation is inexpensive and can be stored for long periods, and be used to provide rapid chitin hydrogel treatment of a hemorrhaging wound without the time delay associated with solubilization and mixing of the components. These characteristics when combine with a hemostatic composition make it ideal for use in field applications, such as in trauma packs for soldiers, rescue workers, ambulance/paramedic teams, firemen, and in early trauma and first aid treatment by emergency room personnel in hospitals and clinics, particularly in disaster situations. A small version may also have utility in first aid kits for use by the general public or by medical practitioners.

The self-contained chitin hydrogel wound dressing or chitin hydrogel-containing bandage comprises a tissue sealing composition comprising a chitin hydrogel complex, which may consist of other chitins or their derivatives with a cross-linking agent, such as glyoxal, gluteraldehyde, PEG succinamide, PEG succimidyl succinate or PEG succimidyl propionate.

When used on human patients, the components are most preferably pathogen-inactivated, purified components. In particular, the components of the present invention, including additives thereto, are treated with a detergent/solvent, and/or otherwise treated, e.g., by pasteurization or ultrafiltration to inactivate any pathogenic contaminants therein, such as viruses. Methods for inactivating contaminants are well-known to those of skill in the art and include, but are not limited to, solvent-detergent treatment and heat treatment. Solvent-detergent treatment is particularly advantageous in that the proteinaceous components are not exposed to irreversible heat-denaturation.

The chitin hydrogel can be, but does not have to be, supplemented in each of the following embodiments with one or more growth factors, drugs, inhibiting compounds (to inhibit the activities of the hydrogel that may interfere with any of the biological activities of the growth factor or drug), and potentiating compounds (to potentiate, mediate or enhance any of the biological activities of the growth factor or drug), compounds which inhibit the breakdown of dyes.

The growth factor may include, e.g., fibroblast growth factor-1, fibroblast growth factor-2 and fibroblast growth factor-4; platelet-derived growth factor; insulin-binding growth factor-1; insulin-binding growth factor-2; epidermal growth factor; transforming growth factor-α; transforming growth factor-β; cartilage-inducing factors -A and -B; osteoid-inducing factor; osteogenin and other bone growth factors; collagen growth factor; heparin-binding growth factor-1; heparin-binding growth factor-2; and/or their biologically active derivatives.

The drug may be an analgesic, antiseptic, antibiotic or other drug(s), such as antiproliferative drugs which can inhibit infection, promote wound healing and/or inhibit scar formation. More than one drug may be added to the composition, to be released simultaneously, or the drug may be released in predetermined time-release manner. Such drugs may include, for example, taxol, tetracycline free base, tetracycline hydrochloride, ciprofloxacin hydrochloride or 5-fluorouracil. The addition of taxol to the chitin hydrogel complex may be particularly advantageous. Further, the drug may be a vasoconstrictor, e.g., epinephrine; or the drug may be added to stabilize the chitin hydrogel seal, e.g., aprotinin. The supplement(s) is at a concentration in the chitin hydrogel such that it will be effective for its intended purpose, e.g., an antibiotic will inhibit the growth of microbes, an analgesic will relieve pain, etc.

Dyes, markers or tracers may be added, for example, to indicate the extent to which the chitin hydrogel may have entered the wound, or to measure the subsequent resorption of the chitin hydrogel, or the dye may be released from the chitin hydrogel in a predetermined, time-release manner for diagnostic purposes. The dyes, markers or tracers must be physiologically compatible, and may be selected from colored dyes, including water soluble dyes, such as toluidine blue, and radioactive or fluorescent markers or tracers which are known in the art. The dyes, markers or tracers may also be compounds which may be chemically coupled to one or more components of the chitin hydrogel. In addition, the marker may be selected from among proteinaceous materials which are known in the art, which upon exposure to proteolytic degradation, such as would occur upon exposure to proteases escaping from wounded tissue, change color or develop a color, the intensity of which can be quantified.

Moreover, when the chitin hydrogel is used to replace or repair wounded or damaged bone or ossified tissue, the composition may also be supplemented with effective amounts of demineralized bone matrix and/or bone morphogenic proteins, and/or their biologically compatible derivatives.

The concentration of the chitin hydrogel and/or hydrating agent(s) of the self-contained chitin hydrogel wound dressing or chitin hydrogel bandage may have a significant effect on the density and setting time of the final matrix. This principle may be used to satisfy specific uses of the self-contained chitin hydrogel-containing wound dressing or bandage in specialized situations. For example, the treatment of an arterial wound may require the chitin hydrogel seal to set very rapidly and with sufficient integrity to withstand pressurized blood flow. On the other hand, when filling deep crevices in a wound, treatment may require the components to fill the wound completely before the chitin hydrogel seal sets.

The Gel Pack Embodiments

In the gel pack embodiment of the self-contained dressing, the chitin components and hydrating agent components are individually contained in independent quick-evaporating gel layers (e.g., methylcellulose/alcohol/water), wherein the two gel layers are separated from each other by an impermeable membrane, and the pair are covered with an outer, protective, second impermeable membrane. The bandage may be coated on the surface that is in contact with the gel in order to insure that the gel pad remains in place during use.

In use, the membrane separating the two gel layers is removed, allowing the two components to mix. The outer membrane is then removed and the bandage is applied to the wound site. This results in a natural inhibition of blood and fluid loss from the wound, and establishes a natural barrier to infection.

In a similar gel pack embodiment, both the hydrating agent, and the plastic film separating the chitin components and the hydrating agent, may be omitted. In operation, the outer impervious plastic film is removed and the bandage applied, as previously described, directly to the wound site. The fluids naturally present at the wound site then hydrate the chitin components to form a hydrogel.

This alternative embodiment of the gel pack has the advantage of being simpler, cheaper, and easier to produce. However, there may be circumstances in which a patient's wounds have insufficient fluid to effectively transform the chitin components into a hydrated gel. In those cases, the hydrating agent must be exogenously supplied, as in the earlier-described gel pack embodiment of the invention.

The Chitin Hydrogel Bandage Embodiments

A chitin hydrogel bandage embodiment is formulated for releasing a necessary supplement to wounded tissue in a patient, wherein the bandage comprises, a layer of dry materials comprising an effective amount of chitin or its derivative to upon hydration form a hydrogel, wherein the layer of dry materials is affixed to the wound-facing surface of the bandage. In one embodiment, the occlusive backing and the physiologically-acceptable adhesive layer are one and the same, if the backing layer is sufficiently adhesive to effectively bind the layer of dry materials.

In another embodiment, a removable, waterproof, protective film is placed over the layer of dry materials and the exposed adhesive surface of the bandage for long-term stable storage. In operation the waterproof, protective film is removed prior to the application of the bandage over the wounded tissue.

The chitin component of the bandage in one embodiment is activated at the time the bandage is applied to the wounded tissue to form a chitin hydrogel by the patient's endogenous fluids escaping from the hemorrhaging wound. Preferably, the chitin hydrogel is hydrated and fluid loss from the wound will be significantly diminished within minutes of application of the bandage to the wounded tissue. Although the speed with which the chitin hydrogel forms and sets may be to some degree dictated by the application, e.g., rapid setting for arterial wounds and hemorrhaging tissue damage, slower setting for treatment of wounds to bony tissue, preferably the chitin hydrogel will form within twenty minutes after application. More preferably, this effect will be evident within ten minutes after application of the bandage. Most preferably, the chitin hydrogel will form within two to five minutes after application. In the embodiment comprising the most rapidly forming chitin hydrogel will be substantially formed within 1–2 minutes, more preferably within 1 minute, and most preferably within 30 seconds after application.

It may be necessary to use pressure in applying the chitin hydrogel bandage until the chitin hydrogel has formed over the wound site.

In the alternative, in situations where fluid loss from the wound is insufficient to provide adequate hydration of the dry chitin components, or where time is of the essence, as in a life-threatening situation, the chitin hydrogel is hydrated by a suitable, physiologically-acceptable liquid prior to application of the bandage to the wounded tissue.

To construct the bandage, the dry materials may be obtained, for example, by lyophilization or freeze-drying, or suitable, commercially-available materials may be utilized. The binding of the dry materials to the adhesive or backing layer may be enhanced by adding a binder, preferably a water soluble binder, to the dry components.

The backing of the chitin hydrogel bandage may be of conventional, non-resorbable materials, e.g., a silicone patch or plastic material; or it may be of biocompatible, resorbable materials, e.g., chitin or its derivatives. The backing material may act as more than a delivery device. Its preferred composition is determined by the desired application of the chitin hydrogel. For example, a non-resorbable backing is appropriate for many external uses, where it provides strength and protection for the chitin hydrogel. In an alternative embodiment, the non-resorbable backing is reinforced, e.g., with fibers, to provide extra strength and durability for the protective covering over the chitin hydrogel.

Subsequent removal of the clot with the backing is acceptable in many situations, such as when the chitin hydrogel bandage is used as a first aid measure until medical assistance becomes available.

In the alternative, the non-resorbable backing may be used to provide strength to the tissue sealing chitin hydrogel seal during its formation, e.g., when the hemorrhaging fluids are escaping under pressure, as in an arterial wound. Yet, if such a wound is internal, it is advantageous to remove the backing from the chitin hydrogel without disturbing the established hydrogel matrix. Therefore, a chitin hydrogel bandage is provided in which the adhesive layer is of a material having a lower tensile or shear strength than that of the chitin hydrogel, permitting removal of the backing without damage to the chitin hydrogel seal or the tissue surrounding the wound.

By comparison, certain internal applications mandate the use of a resorbable backing to eliminate the need for subsequent removal of the dressing. A resorbable material is one which is broken down spontaneously or by the body into components which are consumed or eliminated in such a manner as to not significantly interfere with healing and/or tissue regeneration or function, and without causing any other metabolic disturbance. Homeostasis is preserved. Materials suitable for preparing the biodegradable backing include proteinaceous substances, e.g., fibrin, collagen, keratin and gelatin, or carbohydrate derived substances, e.g., carboxymethylcellulose or cellulose, and/or their biologically compatible derivatives. More preferably, the resorbable material may be thin layer of chitin or chitin hydrogel.

The adhesive layer, if separate from the occlusive backing layer, is selected on the basis of the intended application of the chitin hydrogel, and may comprise conventional adhesive materials. Antiseptic may be added to the adhesive layer.

If the tissue sealing chitin hydrogel is to be removed from the wound with the occlusive backing, such as prior to surgery, the adhesive must be sufficient to affix the dry material layer to the occlusive backing, and to maintain an adhesive capability after hydration which is greater than the tensile or sheer strengths of chitin hydrogel.

If the tissue sealing chitin hydrogel is to remain in position over the wound, but the occlusive backing must be removed after application, the adhesive must be sufficiently sticky to affix the dry material layer to the occlusive backing, but yet have an adhesive capability after hydration which is less than the tensile or sheer strength of the chitin hydrogel. In the alternative, the adhesive layer may be of a material which becomes solubilized or less sticky during hydration of the dry materials, permitting removal of the backing from the chitin hydrogel. In the alterative for such purposes, the dry material layer may be affixed directly to the occlusive bandage.

In another embodiment, the adhesive layer comprises two different adhesives to permit removal after hydration of the occlusive layer without disturbing the tissue sealing chitin hydrogel. Typically, in such a situation the dry, chitin hydrogel is affixed to a specific region of the backing, the "inner region," e.g., the center, with an unencumbered area of adhesive extending beyond the area of dry material, the "outer region."

The outer region of adhesive is affixed directly to the skin or tissue surrounding or adjacent to the wound in such a way that the dry material region of the bandage forms a chitin hydrogel directly over the wound. The adhesive layer on the region of backing which is not covered by the dry material layer of the bandage is sufficient to affix the chitin hydrogel to the tissue surrounding the wound until its physical removal. The adhesive on the outer region must be sufficient to hold the bandage in place, even if fluids are hemorrhaging from the wound under pressure, e.g., an arterial wound.

The inner region of adhesive is sufficiently sticky to affix the dry material layer to the occlusive backing, but yet have an adhesive capability after hydration which is less than the tensile or sheer strength of the chitin hydrogel. In the alternative, the inner region of adhesive is of a material which becomes solubilized or less sticky during hydration of the dry materials, permitting removal of the backing from the chitin hydrogel. In the alterative for such purposes, the dry material layer may be affixed in the inner region directly to the occlusive bandage, with an adhesive layer added only to the outer layer.

Thus, in the two adhesive embodiment, the backing of the chitin hydrogel bandage remains in place affixed to the tissue surrounding the wound until the bandage is physically removed. But upon removal, the backing separates from the chitin hydrogel without disturbing matrix attached to the wound.

The Dual-Encapsulated Embodiments of the Chitin Hydrogel

In yet another embodiment of the chitin hydrogel bandage, an independent hydrating layer comprising an effective amount of carbonated water or physiologically-acceptable buffered hydrating agent, such as PBS, or comparable gel, is contained within a rupturable, liquid-impermeable container. The rupturable, liquid-impermeable container encapsulating the hydrating layer is affixed directly to the above-described occlusive bandage layer or to the above-described adhesive layer adjacent to the occlusive bandage. Affixed to the exposed side (the side which is not attached to the backing or adhesive layer) of the rupturable, liquid-impermeable container encapsulating the hydrating layer is a dry layer of finely-ground, powdered chitin.

The dual layers (the dry layer and the hydrating layer) are together covered on all surfaces not in contact with the occlusive backing or adhesive material affixing the layers to the occlusive backing, with an outer, protective, second impermeable membrane. Thus, in this dual-layer embodiment, the contents are entirely encapsulated within an impermeable container, wherein one side is the occlusive backing material and the other side and all edges are formed by the outer, protective, second impermeable membrane.

In operation, the inner liquid-impermeable container encapsulating the hydrating layer is physically ruptured to release the hydrating material contained therein into the dry chitin layer, resulting in a fully-hydrated chitin hydrogel to provide a natural barrier to infection. The outer, second impermeable membrane retains the released hydrating material in contact with the dry components until a malleable hydrated chitin hydrogel complex forms, at which time the outer membrane is physically removed and the bandage placed over the wound.

In the alternative, the outer membrane may be physically removed, and the dual layers forcefully applied to the wound area in a manner which ruptures the inner liquid-impermeable container and releases the hydrating agent into the dry chitin components to form a chitin hydrogel complex directly on the wounded tissue.

As in other embodiments of the chitin hydrogel bandage, the selected adhesives and backing materials may be determined by the intended application of the bandage. The backing may be removable or resorbable, and the adhesive may have the intended purpose upon removal of the bandage of removing the chitin hydrogel from the wound, or of leaving the chitin hydrogel undisturbed. The adhesive may be a separately bound layer, or the backing may itself act as an adhesive to affix the dry chitin hydrogel.

Additives, such as the previously disclosed growth factors, antibiotics, antiseptics, antiproliferative drugs, etc. may also be included in this embodiment of the chitin hydrogel bandage.

If the hydrating layer contains a liquid supersaturated with gas, the dry material layer will be hydrated as an expandable, foaming, chitin hydrogel. In the alternative, the dry material layer may be supplemented with materials which produce gas, and hence foaming, upon contact with the hydrating agent.

If the hydrating layer is in the form of a gel, such as a quick-evaporating gel layers (e.g., methylcellulose/alcohol/water), the rupture of the surrounding impermeable barrier permits the dry chitin components to directly contact the hydrating layer as disclosed above to produce the chitin hydrogel. The gel layer, in the manner described for a liquid hydrating layer, may comprise any one, or all, of the above-disclosed additives.

In an alternate dual layer embodiment, the chitin hydrogel is delivered as a wound sealing dressing, which need not be affixed to a backing. The components are organized essentially as a capsule within a capsule, wherein the term capsule is used to define a broad concept, rather than a material. The above-described encapsulated hydrating layer is itself contained within a second encapsulating unit, which contains both the dry chitin and the encapsulated hydrating layer.

In operation, the inner, liquid-impermeable container encapsulating the hydrating layer is physically ruptured to release the hydrating material contained therein into the dry chitin component layer, both of which remain completely contained within the outer, second encapsulating unit. The integrity of the outer, second encapsulating unit is not broken when the inner container encapsulating the hydrating layer is physically ruptured.

The mixing of the hydrating layer with the dry chitin components within the outer encapsulating unit results in a fully-hydrated hydrogel, which is then released or expelled onto wounded tissue. To release the chitin hydrogel mass, the outer encapsulating unit is physically cut or torn, either randomly or at a specific location on the surface, e.g., to form a pour spout to direct the flow of the malleable chitin hydrogel onto the wound site.

If the hydrating layer is a agent supersaturated with gas, the mixing of the hydrating agent with the dry chitin hydrogel components results in an expandable foaming mixture, which is then applied to the wounded tissue. The foaming may, in the alternative, be achieved by hydration of the dry component layer.

The Self-Foaming Chitin Hydrogel Embodiments

A self-foaming chitin hydrogel dressing embodiment for treating wounded tissue in a patient is formulated as an expandable foam comprising a hydrogel-forming amount of chitin or its derivatives The previously described chitin hydrogel components are stored in a canister or tank with a pressurized propellant, so that the components are delivered to the wound site as an expandable foam.

Acceptable formulations of the expandable foam embodiment provide the hydrated components of a chitin hydrogel, which in operation expand up to twenty-fold. The extent of expansion of the chitin hydrogel, however, is determined by its intended application.

For example, use of the expandable foam chitin hydrogel dressing within the abdomen provides a chitin hydrogel to provide a barrier to infection while releasing a necessary supplement. However, at the same time the expansion of the foam must be controlled to prevent harmful pressure on undamaged tissue, organs or blood vessels. Such a situation may warrant the use of an expandable foam dressing in which the expansion is limited to only 1- or 2-fold, and not more than 5–10 fold.

By comparison, use of the expandable foam chitin hydrogel dressing to fill gaps within bone, may warrant the use of material which expands at a much greater rate to produce a tight and firm seal over the wounded area. The extent of the expansion of such material may be in the range of above 20-fold, although preferably 10–20 fold, or more preferably 5–10 fold. An expansion of less than 5-fold, including 1- to 2-fold may also be applicable to repair of blood vessels or injured bone, for example in small areas, such as the inner ear. Such an application is particularly suited to the delivery of neurotoxins to the middle ear for the treatment of Meniere's disease.

Like the expansion rate, the set-up time for the formation of the chitin hydrogel using the expandable foam chitin hydrogel dressing is also related to its intended application. Although a set-up time of under 1 minute is appropriate, set-up times of 1–2 minutes, or up to 5 minutes would be acceptable. In circumstances recognizable to one of ordinary skill in the art, a long set-up time of 5–10 minutes, or even up to twenty minutes, may be acceptable in non-life threatening situations.

The delivery devices, e.g., canister, tank, etc., may be developed especially for the present application, or they may be commercially available. The canister may comprise either a single or multiple reservoirs. Separate reservoirs, although more expensive, will advantageously permit the hydrated components to remain separated and stable until they are mixed upon application.

The propellant must be physiologically acceptable, suitable for pharmacological applications, and may include conventionally recognized propellants, for example, $CO_2$, N₂, air or inert gas, such as freon, under pressure. In the alternative, the dry chitin hydrogel components may be supplemented with material(s) which produce gas, and hence foaming, upon contact with the hydrating agent.

Since delivery pressure of the expandable foam chitin hydrogel dressing from the delivery device, when combined with the composition of the chitin hydrogel itself and its set-up time, determines the extent of expansion of the dressing, the delivery pressure is determined by the nature of the wound being treated. Pressure of 1 atmosphere, or less (14.7 lbs/inch$^2$) will provide a low level of expansion and a slower rate of delivery. However, certain situations may warrant a delivery pressure of 1–5 atmospheres, or more. In most cases, the delivery pressure chosen corresponds to that of commercially available canister devices. As an addition factor, the delivery pressure may be important to keep the hydrogel components from clogging delivery lines or devices.

Finally, certain traumatic injuries will be best treated by combining several embodiments of the chitin hydrogel dressing. For example, in serious car accidents or injuries caused by antipersonnel-mines or explosives, the wounds may be not only life-threatening but extensive, involving large, jagged openings in tissue or bone with significant internal damage, often with accompanying serious burns. Such wounds may present numerous severed arteries and blood vessels in addition to extensive areas of wounded tissue. In such wounds, it may be advantageous to first liberally apply a hemostatic agent, and then to wrap the entire area in an embodiment of the chitin hydrogel bandage to support and protect the wounded area, and perhaps release a painkilling and/or antimicrobial composition and slow fluid loss with a vasoconstrictor. Such treatment is particularly advantageous for patients who have suffered extensively burned tissue, until the victim can be transported to a medical facility, or until professional medical assistance can administered. In most instances, additional formulations of the chitin hydrogel dressing will then be applied by the trained personnel for the long-term repair, treatment and protection of the injured tissue.

The following examples are included for illustrative purposes only and are not intended to limit the scope of the invention.

EXAMPLES

Example 1

Antibiotic Release from a Chitin Hydrogel

The suitability of N,O-carboxymethylated chitosan (NOC-chitosan) was investigated as a delivery vehicle for local deposition of antibiotics. NOC-chitosan was purchased from NovaChem (Halifax, Nova Scotia, Canada). NOC-chitosan is water soluble, injectable, biocompatible and naturally resorbed by a mammalian host. It is formed by carboxymethlyation of biomedical grade chitosan. Tetracycline (free base) and ampicillin (free acid)(Sigma Chem., St. Louis, Mo.) and ciprofloxacin-hydrochloride (CIP) (Miles, West Haven, Conn.).

Cylindrical pellets of uniform size (6 mm×3 mm) were prepared containing 50 mg of tetracycline, ciprofloxacin or ampicillin. The in vitro release rates were monitored under two conditions: (i) agitation in a large fluid volume (infinite sink) and (ii) static within a small fluid volume (limited sink). Infinite sink and limited sink conditions approximate Lovely the highest and the lowest release rates expected in physiological settings. Implantation of matrix under a very limited flow situation such as within a bone is simulated in vitro using the limited sink model. Under limited sink conditions, tetracycline continued to elute effective (>32 μg/ml, MIC for *S. aureus* is 1 to 10 μg/ml) concentrations of antibiotic for 42 days. While under infinite sink conditions the duration of release is at least 12 days (250 μg/day). The release kinetics of ciprofloxacin under the limited sink conditions was similar to the tetracycline release kinetics with release rates greater than 800 μg/day at the end of two weeks. These findings suggest that NOC-chitosan is an effective candidate for local antibiotic delivery for 2–6 weeks.

Preparation of Matrices

NOC-chitosan was dissolved in PBS (130 mM NaCl, 20 mM Sodium Phosphate at pH 7.2) at a concentration of 75 mg/ml (7.5% w/v) to make a viscous hydrogel. A homogeneous mixture of NOC-chitosan was prepared by syringe-to syringe mixing.

With 345 mg of antibiotic (tetracycline free base or ampicillin free acid or ciprofloxacin hydrochloride), 655 mg of NOC-chitosan gel was mixed by a syringe to-syringe mixing. The admixed drug-chitosan was placed in a 20 mm×10 mm×3 mm mold and pressed to form a slab. Disks were punched out by using a 6 mm biopsy punch. All experiments were conducted with five replicates. To measure the amount of antibiotic loaded in these disks, the antibiotic-NOC-chitosan and NOC-chitosan-only disks were suspended in 2.0 ml of trypsin overnight. Disks dissolved completely in the trypsin solution and the suspension was diluted in PBS and concentrations of antibiotics were analyzed as described below.

In Vitro Release of Antibiotic

Antibiotic delivery was studied under two different conditions. In the "limited sink" model, a small volume of elute was used which was exchanged at regular intervals. The system was not agitated. The antibiotic-NOC-chitosan disks were placed into a well of a 24 well sterile tissue culture plate (Corning, Corning, N.Y.). PBS (2 ml) was added to each well at time zero and the disks were completely immersed. All release measurements were conducted at 37° C. Elution buffer was exchanged daily and analyzed to measure the concentration of antibiotic released (described below). NOC-chitosan disks with no antibiotic were also tested under similar conditions to ensure a zero base line in the measurements of antibiotics by spectrophotometer.

In the "infinite sink model," a larger eluate volume and continuous agitation were used. Antibiotic-NOC-chitosan disks were suspended in 45 ml of PBS in a 50 ml centrifuge tube kept at 37° C. that was inverted approximately 20 times per minute. The buffer was exchanged daily and analyzed for amount of antibiotic released. For both limited and unlimited sink conditions, disks were visually analyzed for any signs of erosion, swelling and disintegration.

Measurement of Tetracycline and Ciprofloxacin Concentrations

The concentrations of tetracycline as well as ciprofloxacin were measured by spectrophotometry at 340 nm using a microplate reader (Molecular Devices, Sunnyvale, Calif.). A standard curve was prepared using tetracycline hydrochloride and ciprofloxacin hydrochloride covering concentrations from 0 to 200 μg/ml. Ampicillin was measured using BCA reagent and measured at 560 nm after complex formation. One ml of BCA reagent was mixed with 0.1 ml of antibiotic solution and incubated at 37° C. for 30 minutes. Absorbance at 560 nm was measured to quantitate the amount of ampicillin using a standard curve of known concentrations. When necessary the experimental samples were diluted with distilled water to be within the standard concentration range.

Results

Tetracycline delivery from NOC-chitosan disks is shown as a function of time in FIG. 1. The amount of tetracycline in each disk was 50 mg±2 mg. Initially, there was a burst of tetracycline released with 3.1 mg delivered on the first day and 2.9 mg on the second day. The release rates subsequently decrease after day 2 and levels between 2.4–1.3 mg were delivered between day 3 to day 15. The drug level further decreased after day 15 to 650–100 μg/day released between day 16 and day 37. In the sixth week (days 37–42) the amount of tetracycline released was above 65 μg/day. The tetracycline-NOC-chitosan matrix showed no visual signs of erosion for first two weeks. The matrix started disintegrating in the third week and towards the fifth and sixth week the matrix was present in small pieces. The NOC-chitosan matrix containing no antibiotic showed visible signs of dissolution and disintegration after the first day and was completely dissolved on the second day.

Figure 2:
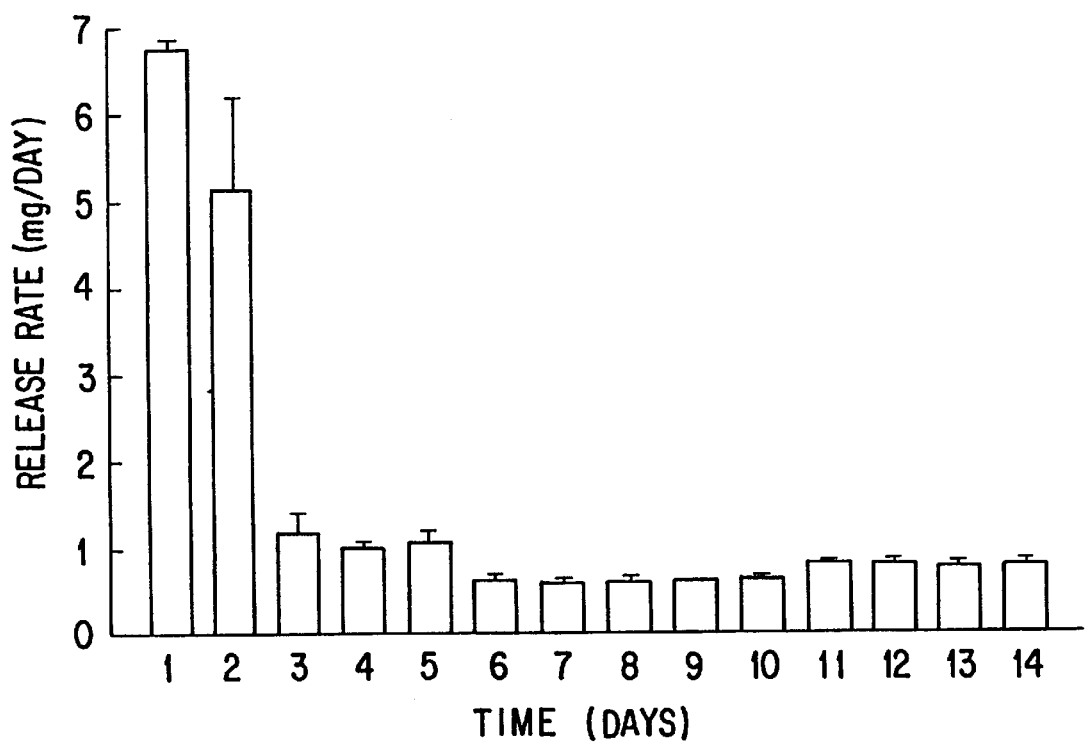
FIG. 2. Tetracycline release from NOC-chitosan matrices under infinite sink conditions. The concentration of NOC-chitosan was 66 mg/ml and the amount of tetracycline in each disk was 50 mg. Error bars represent the standard deviation for n=5.

In order to determine the maximum possible release rate, tetracycline release data was obtained under infinite sink conditions, and are shown in FIG. 2. The initial burst on day 1 released greater than 20 mg (40% of tetracycline loaded) of tetracycline. The release rate decreased dramatically after one day, however, the amount released remained above 2.5 mg/day for day 2 to day 5. The release rates further decreased after that and the release rate were greater than 250 μg/day for an additional 7 days. The matrix had some visible signs of disintegration at the end of 12 days. In contrast to this, the NOC-chitosan-only matrix dissolved completely in one day and no traces of matrix were left. Table 1 shows the time for disintegration of the NOC-chitosan disks and NOC-chitosan-antibiotic disks under limited and infinite sink conditions. The eluent from NOC-chitosan-only matrix in the elution buffer were also analyzed at 340 nm and no absorbance was found.

TABLE 1

Time for disintegration of the FS and FS/antibiotic disks

|  | Limited Sink | Infinite Sink |
| --- | --- | --- |
| NOCC | 2 days | 1 day |
| NOCC-Ciproflaxin | >3 weeks | Not Measured |
| NOCC-Tetracycline | >3 weeks | >10 days |
| NOCC-Ampicillin | 4 days | Not Measured |

Disintegration Time Measured by Daily, Visual Inspection of the Disks.

Figure 3:
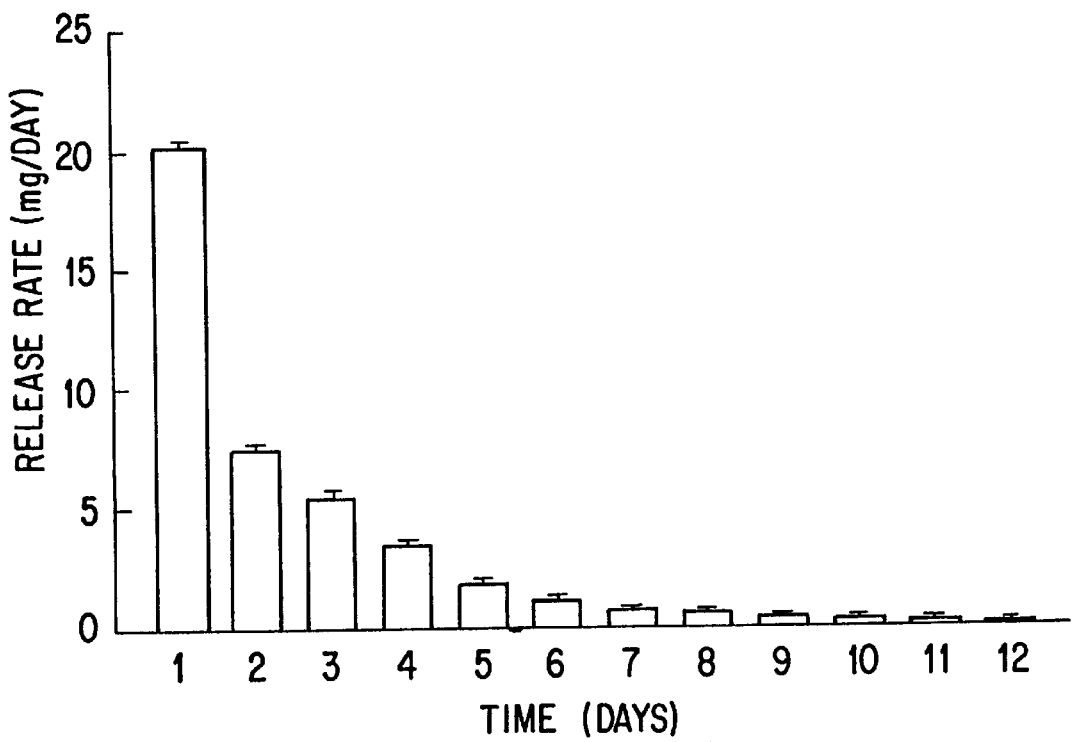
FIG. 3. Ciprofloxacin release from NOC-chitosan matrices under limited sink conditions. The concentration of NOC-chitosan was 66 mg/ml and the amount of ciprofloxacin in each disk was 50 mg. Error bars represent the standard deviation for n=4.

FIG. 3 shows the release rates for ciprofloxacin under limited sink conditions. The amount of ciprofloxacin releasing in the elution buffer is plotted as a function of time. The initial bursts on day 1 and day 2 released 6.7 mg and 5.2 mg respectively. After the second day, the release rates decreased substantially to 1.2–1.0 mg/day for day 3–day 5. After day 5, release rates above 600 μg/day were observed for another 7 days. NOC-chitosan containing ciprofloxacin showed significant signs of swelling visibly and the matrix dimensions were altered with time. In contrast to this, NOC-chitosan-only was completely dissolved in two days. At the end of 12 days the cumulative amount of ciprofloxacin released was about 21.5 mg which is 43% of amount loaded. The matrix still contained 57% of the antibiotic.

Figure 4:
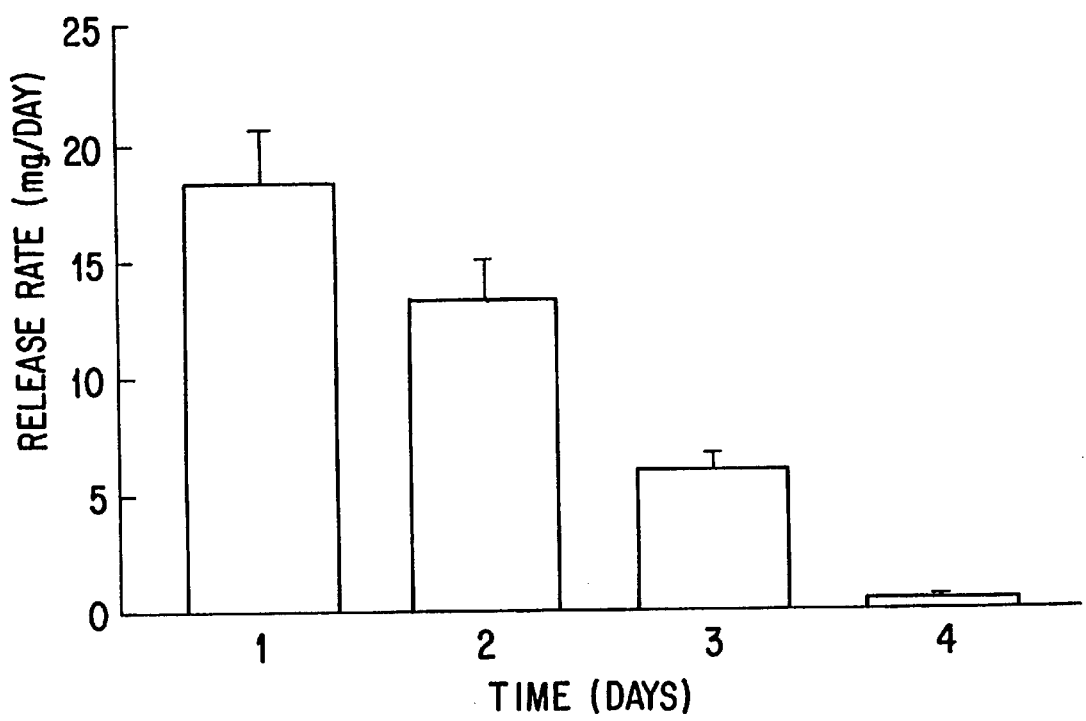
FIG. 4. Ampicillin release from NOC-chitosan matrices under limited sink conditions. The concentration of NOC-chitosan was 66 mg/ml and the amount of ampicillin in each disk was 50 mg. Error bars represent the standard deviation for n=4.

FIG. 4 shows the ampicillin release under limited sink conditions. The initial burst on day 1 released 18.5 mg of ampicillin and all the ampicillin loaded was released in first four days. The matrix completely disintegrated after the release of all the antibiotic loaded.

Discussion

The objective of this study was to develop new techniques to deliver antibiotics for long time periods using a bioresorbable matrix as the delivery system. We chose chitosan as the bioresorbable matrix and studied the release kinetics of broad spectrum antibiotics. Earlier attempts to use plaster of paris (POP) and morselized bone graft matrix have met with limited success (Mackey, D. et al., *Clin. Orthop.* 167:263–268 (1982); McLaren, A. & Miniaci, A., *Trans. Soc. Biomater.* 12:1–2 (1986)). In a more recent paper, Miclau (*J. Orthop. Res.* 11:627–632 (1994)) utilized morselled bone graft and plaster of paris as delivery matrices and measured the release kinetics of antibiotic tobramycin. For the case of bone graft they found 70% of the antibiotic eluted in 24 hours and trace amounts detected after 4 days. Seventeen percent of antibiotic eluted from POP in first day with only trace amounts detected after 4 days.

Other previous attempts to obtain a long duration of antibiotic delivery from bioresorbable carriers have also met with limited success, resulting in delivery periods between 1–5 days (typically measured under limited sink conditions) (Goodson, J. et al., *J. Periodontology* 54(10):575–579 (1983); Greco, F. et al., *J. Biomed. Mat. Res.* 25:39–51 (1991); Sakurai, T. et al., *J. Controlled Release* 18:39–44 (1992)).

In contrast, we formulated the antibiotic-matrix to exploit two characteristics that would contribute to a long duration of delivery. The first was the charge interactions between the drug and the matrix, and the second was insolubility of antibiotics. Tetracycline and ciprofloxacin are both positively charged antibiotics resulting from the large number of amine groups. NOC-chitosan has a net negative charge at physiological conditions (pH 7.4). It would appear that the opposite charges of NOC-chitosan and tetracycline, as well as ciprofloxacin, would result in strong electrostatic binding interactions.

It has been shown before that electrostatic charge interactions can be used to retard the release rates of charged drugs (Singh, M. et al., *Proc. Inter. Symp. Control Bioact. Matter.* 21:300–301 (1994)). Further, it has also been demonstrated that negatively charged matrices can be stabilized using ionic crosslinking with positively charged polypeptides (Singh, M., Ph.D. Thesis: "Electrostatic effects on the release of polypeptides from collagen hydrogels," Univ. of Maryland, Baltimore County, Baltimore, Md. (1994)). This current work supports the earlier study as evidenced by the fact that NOC-chitosan containing positively charged antibiotics (tetracycline and ciprofloxacin) were stable and showed no signs of dissolution for at least 3 weeks under limited sink setting compared with NOC-chitosan-only matrix which degraded in two days.

This was further supported by our results using the negatively charged antibiotic (ampicillin) which did not significantly prolong the integrity of the NOC-chitosan matrix.

The antibiotic forms chosen were insoluble and were loaded as powder in the matrix at a mass which exceeded the volume of the matrix. The antibiotic must therefore dissolve before it can diffuse out of the matrix. The rate of release of antibiotics is a function of dissolution which is very slow thus determining the retarded release rate (Chandrasekaran, S. & Paul, D.,*J. Pharm. Sci.* 71:1399–1402 (1982); Higuchi, T., *J. Pharm. Sci.* 52:1145–1149 (1963)).

The in vitro release experiments were conducted under two different conditions. Under our limited sink conditions, there was no agitation. This would be expected to result in the formation of boundary layer of highly concentrated antibiotic solution surrounding the matrix which would inhibit the release of antibiotics. Also because of the small volume of eluent used under limited sink conditions there may be a saturation induced limitation on the release rate. This is an appropriate model for in vivo circumstances where there is a limited fluid flow, such as inside a bone.

In the second set of release experiments, a larger volume of eluate is used and agitation was provided which enhanced the rate of delivery of antibiotic from the matrix. This higher rate of delivery was probably due to two factors:(a) rate of dissolution of drug has increased due to agitation and (b) since a large value of eluate was employed a very low concentration of antibiotic was maintained in elution buffer which ensures large concentration difference for Fickian diffusion (Crank, J., *The Mathematics of Diffusion*, Clarendon Press, Oxford (1975)). This models in vivo antibiotic delivery situations such as from a vascular graft or from orally ingested tablets where there is a lot of fluid flow and agitation. The data obtained using these two models provides estimates of the lower and upper ranges of release kinetics expected in a physiological setting depending on the site of implantation.

When tested under limited sink conditions, tetracycline delivery was achieved for six weeks (amount of tetracycline released >50 $\mu$g/day). For most pathogens an effective tetracycline concentration is in the range of 1–100 $\mu$g/ml (Howard, B., *Clinical and Pathogenic Microbiology*, C. V. Mosby Company, St. Louis (1987)). For example, in the case of periodontal treatment the 10–20 $\mu$g/ml level of tetracycline in the gingival crevicular fluid of patients was observed to inhibit the collagenase activity as well as bacterial growth (Golub, L. et al., *J. Amer. Dental Assoc.* 125:163–171 (1994)). For the case of osteomyelitis one of the main pathogens is *S. aureus* which is inhibited at tetracycline concentrations of 1–10 $\mu$g/ml (Gentry, L., *Inf. Disease Clinics of North Am.* 4:485–499 (1990)). At the end of 6 weeks, 20% of the tetracycline still remained in the disk under limited sink conditions indicating that it will continue to deliver even after 6 weeks. Under the infinite sink conditions, where the rate of dissolution is enhanced due to agitation, the amount of tetracycline releasing on the end of 12 days was 450 $\mu$g and only 10% of tetracycline loaded was remaining in the disk. Based on this one would expect a protection from bacterial infection for at least 12 days under the worst in vitro model conditions. Depending on the site of insertion of the matrix, the release rates can be expected to lie anywhere between these two limits.

We expect minimum effective treatment duration of 12 days and maximum duration of at least 42 days based on our in vitro models. Similar results can also be expected for ciprofloxacin from NOC-chitosan matrices. Ciprofloxacin is highly effective against the osteomyelitis pathogens (AEC for *S. aureus* and *P. aeruginosa* are 0.5–1 $\mu$g/ml) and many clinical trials have confirmed the efficacy and safety of ciprofloxacin as a treatment for osteomyelitis (Gentry (1990), supra).

For both the antibiotics, tetracycline and ciprofloxacin, an initial dump of antibiotics was observed during the first two days. Under limited sink settings (more realistic for osteomyelitis), 12–24% of loaded antibiotic released in the first two days. It has been shown (Gristina, A. et al., "Bacteria and Biomaterials," in *Implantation Biology (The Host Response and Biomedical Devices)*, R. Greco, ed., CRC Press, Ann Arbor (1994), pp. 131–148) that once bacteria colonize a surface, a hundred fold higher concentration of antibiotic than MIC (minimum inhibitory concentration) may be needed to inhibit the bacterial growth from the colonized surface. For this reason, therapeutic success should be possible using NOC-chitosan antibiotic delivery system as a very high dosage (about 100–500 times MIC) is delivered initially followed by a slow sustained delivery over a long time period.

Of note is that chemical crosslinking with glyoxal or glutaraldehyde increases the stability of the matrix irrespective of the amount of antibiotic loaded (Thacharodi, D. & Rao, K., *Int'l J. Pharmaceutics* 96:33–39 (1993)). However, crosslinked matrices are not injectable and they take longer to degrade in a physiological setting. Methods to produce injectable crosslinked chitosan—antibiotic systems are being reduced to practice. Moreover, the effectiveness of NOC-chitosan—antibiotic system in the treatment of acute and chronic osteomyelitis in an animal model is being evaluated.

The objective of this work was to investigate injectable and resorbable antibiotic delivery systems which can provide prolonged therapy by a single administration. We have demonstrated here that NOC-chitosan can provide sustained release of effective concentrations of antibiotics over prolonged time periods. This system should be very effective in treatment of chronic osteomyelitis.

Example 2

Thrombin-Sensitive Plasma Protein Release from a Chitin Hydrogel

Factor IX (FIX) is a plasma glycoprotein that plays a pivotal role in blood coagulation. A congenital X-linked deficiency of biologically active FIX results in hemophilia B (Christmas disease), a potentially life-threatening bleeding disorder. The existing treatment is repeated intravenous infusion of FIX concentrate to stop bleeding episodes. The duration of replacement therapy varies from single injections for minor hemorrhagic events to multiple doses over a few weeks for major surgery. To date, prophylaxis has been achieved only through repeated intravenous injections, but little has been reported on controlled release of FIX.

This example utilized a commercially available, negatively charged derivitive, N,O-carboxymethylated chitosan (NOC-chitosan). Chitosan and NOCC hydrogels have large mesh sizes which provide little diffusional retardation for drug release. The mesh size can be decreased by combining negatively charged NOCC with positively charged polylysine (PL) (Singh M., Ph.D. Thesis: *Electrostatic effects on release of polypeptides from collagen hydrogels*, Univ. of Maryland, Baltimore, Md. (1994)) to retard the diffusional mobility of the diffusing species. The present example discloses the release kinetics of dextran (a model molecule) and FIX from NOC-chitosan and NOC-chitosan-PL matrices in vitro.

Materials and Methods

NOC-chitosan was obtained from NovaChem (Halifax, NS, Canada). Poly-L-lysine (PL) was purchased from Sigma Chemical Co. (St. Louis, Mo.). Dextran-fluorescein (DEXF, MW 70,000) was purchased from Molecular Probes (Eugene, Oreg.). FIX was prepared by two chromatographic steps followed by immunoaffinity chromatography as described previously (Menache, D. et al., "Coagulation Factor IX (human)," in Hemophilia and von Willebrand's Disease in the 1990's, Lusher and Kessler, eds., Elsevier Science Publishers (1991).

Methods

A. Preparation of delivery matrices

An 8% NOC-chitosan gel was prepared by suspending 800 mg of NOC-chitosan in 9.2 ml of an isotonic elution buffer. NOC-chitosan gel (4 g) was combined with 1 ml of DEXF solution (25 mg/ml) in the same buffer using syringe-to-syringe mixing. The resulting mixture contained NOC-chitosan (62 mg/ml) and DEXF (5 mg/ml). Using this technique, NOC-chitosan (26 mg/ml) was prepared with the same concentration of DEXF. To prepare a composite matrix of NOC-chitosan and PL, 40 mg of PL was added to 1 ml of DEXF solution and mixed with 4 g of NOC-chitosan gel. NOC-chitosan matrices containing FIX (625 units/matrix) were prepared with FIX concentrate instead of DEXF.

B. Release Experiments i. DEXF release experiment

One ml of NOC-chitosan-DEXF admixed matrix was placed in a 4 ml cylindrical vial. In vitro release measurements were performed by placing 1 ml of elution buffer on top of the matrix and incubating the vial at 37° C. The buffer was removed every 24 hours and replaced with fresh buffer. DEXF concentration was determined by comparing the UV absorbance at 490 nm with that of a standard curve of DEXF. All release experiments were performed in triplicate.

ii. FIX release experiment

FIX release experiments were conducted using two conditions: (i) no swelling/no erosion and (ii) swelling and erosion. A 0.45 m pore size filter insert (Millipore, Bedford, Mass.) was filled with 0.65 ml of drug admixed matrix. For non-swelling conditions, a plastic cap was placed over the free surface so the matrix could not swell and drug could diffuse only through the filter. For swelling conditions, a plastic cap was placed over the membrane to permit matrix swelling and allow drug diffusion only through the free surface. Each filter insert was submerged in 5 ml of elution buffer in a 50 ml centrifuge tube. Every 24 hours the buffer was removed, replaced with fresh buffer, and analyzed for FIX antigen by ELISA and for FIX clotting activity by an one-stage APTT (Activated Partial Thromboplastin Time) assay.

Results and Discussion

Figure 5:
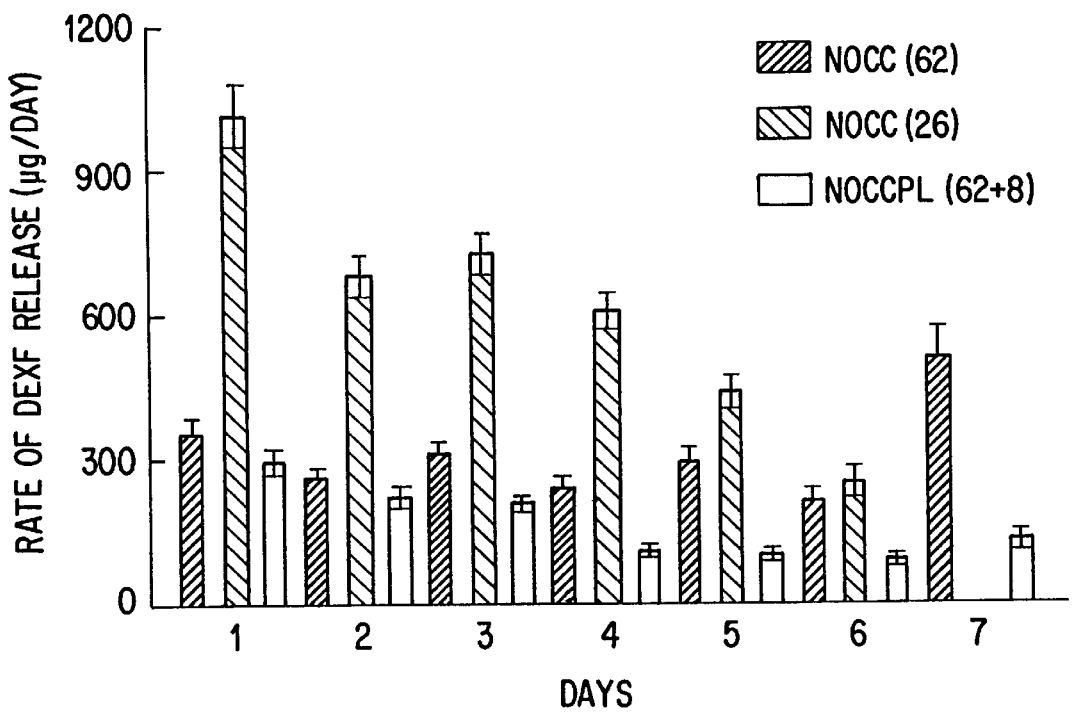
FIG. 5. Release of DEXF from NOC-chitosan (62 mg/ml), NOC-chitosan (26 mg/ml) and NOC-chitosan-PL (62+8 mg/ml) composite matrix.

FIG. 5 shows the release of DEXF from NOC-chitosan and NOC-chitosan-PL matrices. For NOC-chitosan (26 mg/ml), over 80% of the DEXF was released in 7 days, suggesting that diffusional resistance was low at this NOC-chitosan concentration (based on Fick's law). A higher concentration of NOC-chitosan (smaller mesh size) would be expected to release DEXF more slowly, and in fact we found that only 40% of the DEXF was released from NOC-chitosan (62 mg/ml) in 7 days. A composite of NOC-chitosan (62 mg/ml) and PL (8 mg/ml) released DEXF more slowly than NOC-chitosan alone: only 25% was released in 7 days.

The slower rate of release obtained from the latter two matrices is probably due to the combined effect of diffusional hindrance and increase in pathlength on swelling (Singh M., Ph.D. Thesis: *Electrostatic effects on release of polypeptides from collagen hydrogels*, Univ. of Maryland, Baltimore, Md. (1994)).

The molecular weight of FIX (56 kDa) is similar to that of the DEXF (70 kDa) employed here. NOC-chitosan at 62 mg/ml and NOC-chitosan-PL could thus be suitable for delivery of FIX. We have not yet tested the swelling of the chitin hydrogel matrix, when it is implanted intramuscularly or subcutaneously. However, to determine the potential influence of swelling on release rates, we measured FIX release from these matrices under conditions of free swelling and no swelling.

Figure 6:
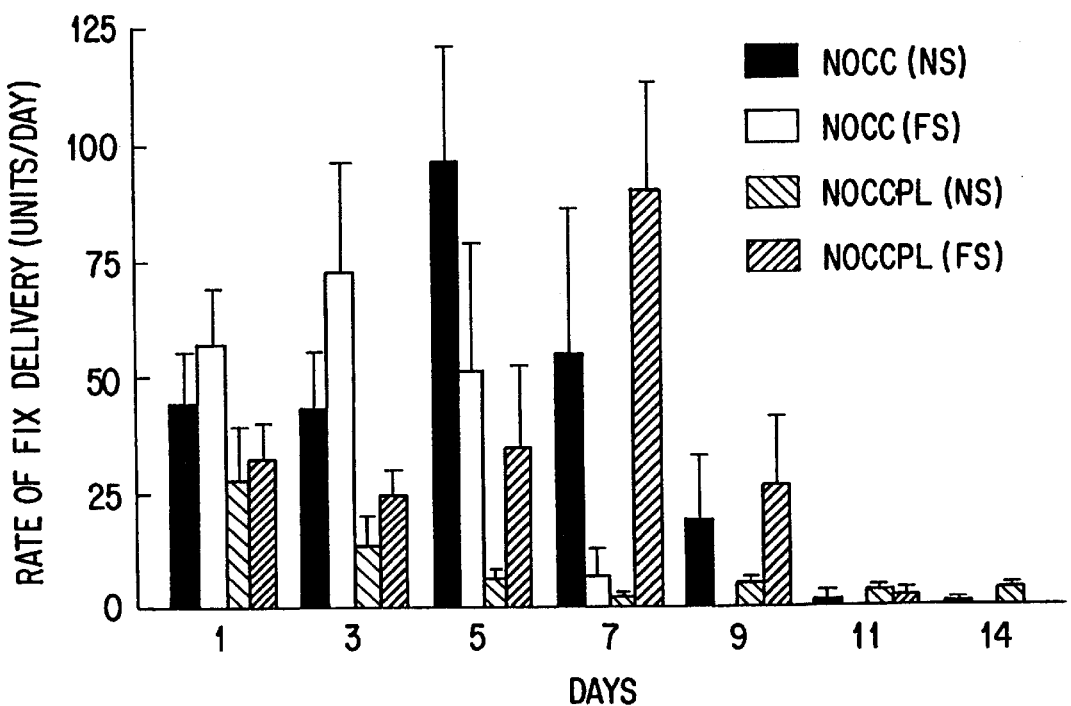
FIG. 6. Release of FIX from NOC-chitosan (62 mg/ml) and NOC-chitosan-PL (62+15 mg/ml) composite matrix. Two conditions of no swelling (NS) and free swelling (FS) are shown here as described in the text. Elution buffers from alternate days were analyzed by ELISA.

FIG. 6. shows the release of FIX (625 units) from NOC-chitosan (62 mg/ml) and NOC-chitosan-PL (62 mg/ml+15 mg/ml) with and without matrix swelling. The NOC-chitosan-PL composite matrix released FIX at a slower rate than NOC-chitosan alone. In all cases, except NOC-chitosan-PL without swelling, all of the FIX was released within 2 weeks. The NOC-chitosan-PL matrix (no swelling) released only 60% of the FIX in 2 weeks, and additional slow release might be possible. For prophylactic treatment of hemophilia B, at least 1% of normal FIX plasma levels are needed. In a 65 kg person, 25 units/day of FIX would be required to enter the blood stream. FIG. 6. indicates that NOC-chitosan can maintain delivery above this level for at least 5 days. The composite matrix can deliver amounts greater than 25 units for at least 9 days under free swelling conditions. The released samples were analyzed for Factor IX activity: the ratio of activity to antigen was 0.5–1.0.

Conclusions

In vitro data indicates that is possible to obtain biologically active FIX release from NOC-chitosan and NOC-chitosan-PL composite matrices over a period of 5–10 days. Therefore, it is predicted that in vivo release would be sufficient to deliver biologically relevant FIX for prophylactic treatment of hemophilia B.

Example 3

In Vivo Release of Factor IX from a Chitin Hydrogel

Based upon the successful in vitro data presented in Example 2, we tested the apparent ability to obtain the in vivo release of biologically active FIX from NOC-chitosan and NOC-chitosan-PL composite matrices over a period of 5–10 days. Typically, the protein and polymers are mixed together in the following way: 4.5 gram of polymer gel is placed in one syringe; 70 mg of freeze-dried Factor IX powder is placed in another syringe. The two syringes are attached to ports of a three-way stopcock with leurlock connections, and mixing is performed by passing the materials several times from syringe to syringe. The mixed polymer-protein hydrogel is injected into a body compartment (intradermal, subcutaneous, intramuscular, intraperitoneal) for the purpose of providing sustained release of the protein and absorption into the blood stream.

A preliminary short term in vivo experiment showed that 200 U of FIX, formulated alone or in NOC-chitosan and NOC-chitosan-PL composite matrices, and injected subcutaneously into an animal resulted in lower peak plasma levels (1 U/ml) than achieved by intravenous (56 U/ml) or subcutaneous (3.2 U/ml) injection of Factor IX alone. The peak plasma levels appeared later when the FIX was delivered in NOC-chitosan and NOC-chitosan-PL, and appeared to decline less rapidly. After 48 and 72 hours, the plasma levels of animals (mice) injected with FIX in NOC-chitosan and NOC-chitosan-PL hydrogels were 2 to 3 times higher than those of comparable animals treated with intravenous or subcutaneous injections of FIX alone. After 72 hours, the bioavailability of subcutaneous FIX was 16%, while that of FIX injected subcutaneously in NOC-chitosan and NOC-chitosan-PL was 5.5% and 8.7%, respectively. Thus, it would appear that subcutaneous release of Factor IX from NOC-chitosan and NOC-chitosan-PL hydrogels may provide practical prophylactic treatment for hemophilia B.

What is claimed is:

1. A composition of matter that provides sustained release of proteins, said composition comprising a covalently cross-linked N,O-carboxymethyl chitosan hydrogel having a protein to be delivered incorporated therein in sufficient concentration to provide said sustained release.

2. The composition of claim 1, wherein said protein is selected from the group consisting of plasma proteins and osteogenic proteins.

3. The composition of claim 2, wherein said plasma proteins are selected from the group consisting of Factor IX, Factor VIII, and mixtures thereof.

4. The composition of claim 2, wherein said osteogenic protein comprises bone morphogenic protein.

5. The composition of claim 4, further comprising a bone growth promoting substance selected from the group consisting of bone marrow cells, bone chips, hydroxyapatite, and mixtures thereof.

6. The composition of claim 1, further comprising at least one growth factor to be delivered incorporated therein in a sufficient concentration to provide sustained release of said growth factor in addition to the sustained release of said protein.

7. A method of providing sustained release of proteins to a subject by administering to the subject a composition comprising a covalently cross-linked N,O-carboxymethyl chitosan hydrogel having a protein to be delivered incorporated therein in a sufficient concentration to provide said sustained release.

8. The method of claim 7, wherein said protein is selected from the group consisting of plasma proteins and osteogenic proteins.

9. The method of claim 8, wherein said plasma protein is selected from the group consisting of Factor IX, Factor VIII, and mixtures thereof.

10. The method of claim 7, wherein said subject has a plasma protein deficiency.

11. The method of claim 10, wherein said disorder is selected from the group consisting of Hemophilia B and Hemophilia A.

12. The method according to claim 7, wherein said composition further comprises a t least one growth facto r to be delivered incorporated therein in a sufficient concentration to provide sustained release of said growth factor.

13. The method according to claim 8, wherein said osteogenic protein comprises bone morphogenic protein.

14. A method of promoting wound healing comprising administering to the wound a composition comprising a covalently cross-linked N,O-carboxymethyl chitosan hydrogel having at least one therapeutically effective protein to be delivered incorporated therein in a sufficient concentration to provide said sustained release of said protein to said wound.

15. The method according to claim 14, wherein said composition administered to said wound further comprises a resorbable backing selected from the group consisting of proteinaceous substances and carbohydrate-derived substances.

16. The method according to claim 15, wherein said proteinaceous substances are selected from the group consisting of fibrin, collagen, keratin, and mixtures thereof.

17. The method according to claim 15, wherein said carbohydrate-derived substance is chitin.

18. The method according to claim 14, wherein said composition is in the form of an expandable foam.

19. The method according to claim 14, wherein said composition further comprises at least one growth factor to be delivered incorporated therein in a sufficient concentration to provide sustained delivery of said growth factor.

20. The method according to claim 19, wherein said wound is in a hard tissue.

21. The method according to claim 20, wherein said hard tissue is bone.

22. The method according to claim 21, wherein said protein comprises an osteogenic protein.

23. The method according to claim 22, wherein said osteogenic protein comprises a bone morphogenic protein.

24. The method according to claim 23, wherein said composition further comprises a bone growth promoting substance selected from the group consisting of bone marrow cells, bone chips, hydroxyapatite, and mixtures thereof.

25. A wound dressing composition for treatment of wounded tissue, said composition comprising a covalently cross-linked N,O-carboxymethyl chitosan hydrogel; and a resorbable backing consisting essentially of therapeutically effective proteinaceous substances.

26. The composition according to claim 25, wherein said N,O-carboxymethyl chitosan hydrogel is in the form of a dry material which forms a N,O-carboxymethyl chitosan hydrogel upon hydration.

27. The composition according to claim 26, wherein said dry material comprises a freeze dried N,O-carboxymethyl chitosan hydrogel.

28. The composition of claim 25, wherein said proteinaceous substances are selected from the group consisting of fibrin, fibrinogen, collagen, keratin, and mixtures thereof.

29. The composition according to claim 25, which hydrogel further comprises a growth factor.

30. The composition of claim 26, further comprising a proteinaceous substance.

31. The composition of claim 30, wherein said wound is an internal wound.

32. The composition of claim 30, wherein said proteinaceous substance is selected from the group consisting of fibrin, fibrinogen, collagen, keratin, and mixtures thereof.

* * * * *